(12) United States Patent
Xu et al.

(10) Patent No.: US 11,427,773 B2
(45) Date of Patent: Aug. 30, 2022

(54) CATALYTIC CRACKING PROCESS FOR PRODUCING ISOBUTANE AND/OR LIGHT AROMATICS IN HIGH YIELD

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Youhao Xu, Beijing (CN); Xin Wang, Beijing (CN); Yuying Zhang, Beijing (CN); Tao Liu, Beijing (CN); Xuhui Bai, Beijing (CN); Lishun Dai, Beijing (CN); Zhigang Zhang, Beijing (CN); Jialin Liang, Beijing (CN); Nan Jiang, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

(*) Notice: Subject to any disclaimer, the term of this patent is extended or adjusted under 35 U.S.C. 154(b) by 0 days.

(21) Appl. No.: 16/756,424

(22) PCT Filed: Oct. 22, 2018

(86) PCT No.: PCT/CN2018/111179
§ 371 (c)(1),
(2) Date: Apr. 15, 2020

(87) PCT Pub. No.: WO2019/080791
PCT Pub. Date: May 2, 2019

(65) Prior Publication Data
US 2020/0239791 A1    Jul. 30, 2020

(30) Foreign Application Priority Data

Oct. 26, 2017 (CN) .......................... 201711022235.0

(51) Int. Cl.
*C10G 69/04* (2006.01)
*C07C 4/06* (2006.01)
(Continued)

(52) U.S. Cl.
CPC ................ *C10G 69/04* (2013.01); *C07C 4/06* (2013.01); *C10G 11/05* (2013.01); *C10G 11/182* (2013.01);
(Continued)

(58) Field of Classification Search
CPC ...... C10G 69/04; C10G 11/05; C10G 11/182; C10G 11/18; C10G 11/185; C10G 11/187;
(Continued)

(56) References Cited

U.S. PATENT DOCUMENTS 2,279,550 A * 4/1942 Benedict ................ C10G 69/04
                                                        208/57
3,684,694 A * 8/1972 Hanson ................... C10G 65/12
                                                        208/89
(Continued)

FOREIGN PATENT DOCUMENTS

CN        1232069 A     10/1999
CN      104178212 A     12/2014
(Continued)

*Primary Examiner* — Michelle Stein
(74) *Attorney, Agent, or Firm* — Novick, Kim & Lee, PLLC; Allen Xue

(57) ABSTRACT

Disclosed is a catalytic cracking process for producing isobutane and/or light aromatics in high yield, comprising the steps of: a) providing a catalytic cracking feedstock oil having a polycyclic naphthene content of greater than about 25 wt %; b) subjecting the catalytic cracking feedstock oil to
(Continued)

a first catalytic cracking reaction and a second catalytic cracking reaction sequentially under different reaction conditions to obtain a catalytic cracking product; c) separating the resulting catalytic cracking product to obtain a liquefied gas fraction comprising isobutane and a gasoline fraction comprising light aromatics; and d) optionally, recovering isobutane from the liquefied gas fraction and/or recovering light aromatics from the gasoline fraction. The process can enable the production of isobutane and/or light aromatics in high yield.

18 Claims, 3 Drawing Sheets

(51) Int. Cl.
C10G 11/05 (2006.01)
C10G 11/18 (2006.01)
C07C 9/12 (2006.01)

(52) U.S. Cl.
CPC ........ C07C 9/12 (2013.01); C10G 2300/1096 (2013.01); C10G 2400/28 (2013.01); C10G 2400/30 (2013.01)

(58) Field of Classification Search
CPC ........ C10G 2300/1096; C10G 2400/30; C10G 51/026; C10G 69/00; C07C 4/06; C07C 9/12
See application file for complete search history.

(56) References Cited

U.S. PATENT DOCUMENTS

| | | |
|---|---|---|
| 5,154,818 A | 10/1992 | Harandi et al. |
| 5,582,714 A * | 12/1996 | Forte ................ C10G 21/16 208/227 |
| 5,685,972 A | 11/1997 | Hye et al. |
| 6,210,561 B1 | 4/2001 | Bradow et al. |
| 6,495,028 B1 * | 12/2002 | Xu ................ C10G 11/18 208/118 |
| 2006/0231459 A1 * | 10/2006 | Swan, III ................ C10L 1/08 208/106 |
| 2008/0078695 A1 * | 4/2008 | Sexton ................ C10G 11/187 208/120.1 |
| 2011/0062054 A1 * | 3/2011 | Gao ................ C10G 11/18 208/57 |
| 2013/0015102 A1 * | 1/2013 | Yanagawa ................ B01J 29/18 423/700 |
| 2013/0118951 A1 * | 5/2013 | Komalarajun ....... C10G 21/003 73/61.59 |
| 2017/0002279 A1 * | 1/2017 | Brown ................ C10G 69/04 |

FOREIGN PATENT DOCUMENTS

| | | |
|---|---|---|
| CN | 104418686 A | 3/2015 |
| CN | 104560166 A | 4/2015 |
| CN | 104711022 A | 6/2015 |
| JP | H08269464 A | 10/1996 |
| RU | 2563637 C2 | 9/2015 |

* cited by examiner

CATALYTIC CRACKING PROCESS FOR PRODUCING ISOBUTANE AND/OR LIGHT AROMATICS IN HIGH YIELD

CROSS REFERENCE TO RELATED APPLICATIONS

The present application is the U.S. national stage application of PCT international application PCT/CN2018/111179, filed on Oct. 22, 2018, which claims the priority of the Chinese Patent Application No. 201711022235.0, titled "Catalytic cracking process for producing isobutane and/or light aromatics in high yield", filed on Oct. 26, 2017, before the Chinese Patent Office, the contents of which are incorporated herein by reference in their entirety.

TECHNICAL FIELD

The present application relates to the field of catalytic cracking, particularly to a catalytic cracking process for producing isobutane and/or light aromatics in high yield.

BACKGROUND ART

Among aromatics, benzene, toluene and xylene (i.e. BTX) are important chemical raw materials, in which benzene can be used in the synthesis of products such as styrene, phenol, aniline and the like, toluene can be used as an excellent solvent for organic synthesis and is an ideal raw material for the synthesis of cresol; and among xylenes, o-xylene, m-xylene and p-xylene are basic raw materials for organic synthesis. Isobutane is an important chemical raw material that can be used in the alkylation reaction with $C_3$-$C_5$ olefins for producing alkylate oil; used in the co-oxidation reaction with propylene for producing propylene oxide (PO) along with tert-butyl alcohol (TBA) or for producing methyl tert-butyl ether (MTBE); or used in the dehydrogenation reaction of isobutane for producing isobutene. With the development of the chemical industry, the market demand for BTX and isobutane is increasing, and it is one of the targets of the development of current chemical technology to expand the sources of BTX and isobutane.

Conventional catalytic cracking processes are mainly used for producing gasoline, and there is a breakthrough that a yield of the gasoline of 50 wt % or more can be achieved, which meets the requirement of unleaded gasoline, and improves the octane number of the gasoline. However, the increase of the octane number of gasoline, no matter by adjusting process conditions or by using a novel zeolite catalyst, is accomplished by increasing the olefin content in the gasoline. At present, the olefin content in catalytic cracking gasoline can reach 35-65 wt %, which is far from the requirement of the National Standard of China on the olefin content. The olefin content in the liquefied gas composition is even higher, and can be about 70 wt %, where the content of butene is several times that of isobutane, and thus it is difficult to be used as a raw material in alkylation.

U.S. Pat. No. 5,154,818A discloses a process for producing high octane gasoline at a higher yield by catalytic cracking of multiple raw materials, in which a light hydrocarbon raw material is contacted with a spent catalyst in a first reaction zone of a conventional riser reactor to perform aromatization and oligomerization reactions, the resultant oil gas is sent to a second reaction zone along with a heavy hydrocarbon raw material to contact with a regenerated catalyst to perform cracking reactions, the resultant oil gas and a spent catalyst are separated in a disengager, the oil gas is sent to a separation system for separation, after being stripped a part of the spent catalyst is recycled to the first reaction zone, and the other part of the spent catalyst is sent to a regenerator for regeneration by burning the coke, and the hot regenerated catalyst is recycled to the second reaction zone for reuse.

U.S. Pat. No. 5,685,972A discloses a process for producing BTX from catalytic cracking naphtha, in which the raw materials used are catalytic cracking naphtha and coking naphtha, and the catalyst used is preferably ZSM-5 or a catalyst with a hydrogenation functional component.

Chinese Patent Application Publication CN104560166A discloses a catalytic conversion process, in which a catalytic cracking light cycle oil is split into a light fraction and a heavy fraction, the heavy fraction is subjected to a hydrotreatment to obtain a hydrogenated heavy fraction, the light fraction and the hydrogenated heavy fraction are separately sent to a secondary riser reactor of the catalytic cracking apparatus, and a heavy petroleum hydrocarbon is sent to a main riser reactor of the catalytic cracking apparatus. In the process, the harsh conditions required for the catalytic cracking reaction of different fractions of the light cycle oil can be optimized and satisfied to a maximum extent, so that a catalytic cracking gasoline with high octane number can be produced to a maximum extent.

Chinese Patent Application Publication CN1232069A discloses a catalytic conversion process for producing isobutane and gasoline rich in isoparaffin, which has the advantages of improved heavy oil processing capacity, reduced yield of dry gas and slurry oil, greatly reduced contents of olefins and sulfur in gasoline, and further reduced energy consumption of equipment.

However, there remains a need in the art for a catalytic cracking process that can further increase the yield of isobutane and/or light aromatics.

SUMMARY OF THE INVENTION

It is an object of the present application to provide a novel catalytic cracking process which can be used to produce isobutane and/or light aromatics in high yield.

In order to achieve the above object, the present application provides a catalytic cracking process comprising the steps of:

a) providing a catalytic cracking feedstock oil having a polycyclic naphthene content of greater than about 25 wt %, based on the weight of the catalytic cracking feedstock oil;

b) contacting the catalytic cracking feedstock oil with a catalytic cracking catalyst in a catalytic cracking reactor, and subjecting the mixture to a first catalytic cracking reaction and a second catalytic cracking reaction sequentially under different reaction conditions to obtain a catalytic cracking product;

c) separating the resulting catalytic cracking product to obtain a liquefied gas fraction comprising isobutane and a gasoline fraction comprising light aromatics; and d) optionally, recovering isobutane from the liquefied gas fraction and/or recovering light aromatics from the gasoline fraction.

In a preferred embodiment, said separation in step c) also produces a light cycle oil fraction, a heavy cycle oil fraction, and optionally a slurry oil, and said process further comprises the steps of:

e) subjecting at least a portion of the light cycle oil fraction, the heavy cycle oil fraction, and the optional slurry oil obtained in the step c) to a hydrotreatment to obtain a hydrogenated tail oil; and f) recycling at least a portion of the resulting hydrogenated tail oil to the catalytic cracking reactor.

In certain preferred embodiments, said step a) further comprises subjecting an initial feedstock oil having a polycyclic naphthene content of no greater than about 25 wt % to a pretreatment to obtain the catalytic cracking feedstock oil having a polycyclic naphthene content of greater than about 25 wt %.

Further preferably, the pretreatment includes aromatics extraction and/or hydrotreatment.

In a preferred embodiment, the first catalytic cracking reaction is carried out under the following conditions: a reaction temperature between about 520° C. and about 620° C., a reaction time between about 0.5 seconds and about 3.0 seconds, and a catalyst-to-oil ratio by weight between about 3:1 and about 15:1; and, the second catalytic cracking reaction is carried out under the following conditions: a reaction temperature between about 480° C. and about 600° C., a reaction time between about 2 seconds and about 30 seconds, and a catalyst-to-oil ratio by weight between about 3:1 and about 18:1.

In a preferred embodiment, the hydrotreatment is carried out under the following conditions: a hydrogen partial pressure between about 6.0 MPa and about 30.0 MPa, a reaction temperature between about 300° C. and about 450° C., a liquid hourly space velocity between about 0.1 $h^{-1}$ and about 10.0 $h^{-1}$, and a hydrogen-to-oil ratio by volume between about 300 $Nm^3/m^3$ and about 3000 $Nm^3/m^3$.

The catalytic cracking process according to the present application may provide one or more of the following advantages:

1. the feedstock oil rich in polycyclic naphthenes or the feedstock oil capable of being modified to have a high polycyclic naphthene content through pretreatment can be fully utilized, so that a high efficient utilization of the feedstock oil can be realized;

2. the isobutane content in the liquefied gas product can be effectively improved; and 3. a gasoline yield of more than 40 wt % can be obtained, and the light aromatics content in the gasoline product can be improved.

Additional features and advantages of the present invention will be described in detail in the Detailed Description hereinbelow.

BRIEF DESCRIPTION OF THE DRAWINGS

The drawings, forming a part of the present description, are provided to help the understanding of the present application, and should not be considered to be limiting. The present application can be interpreted with reference to the drawings in combination with the Detailed Description hereinbelow. In the drawings.

Figure 1:
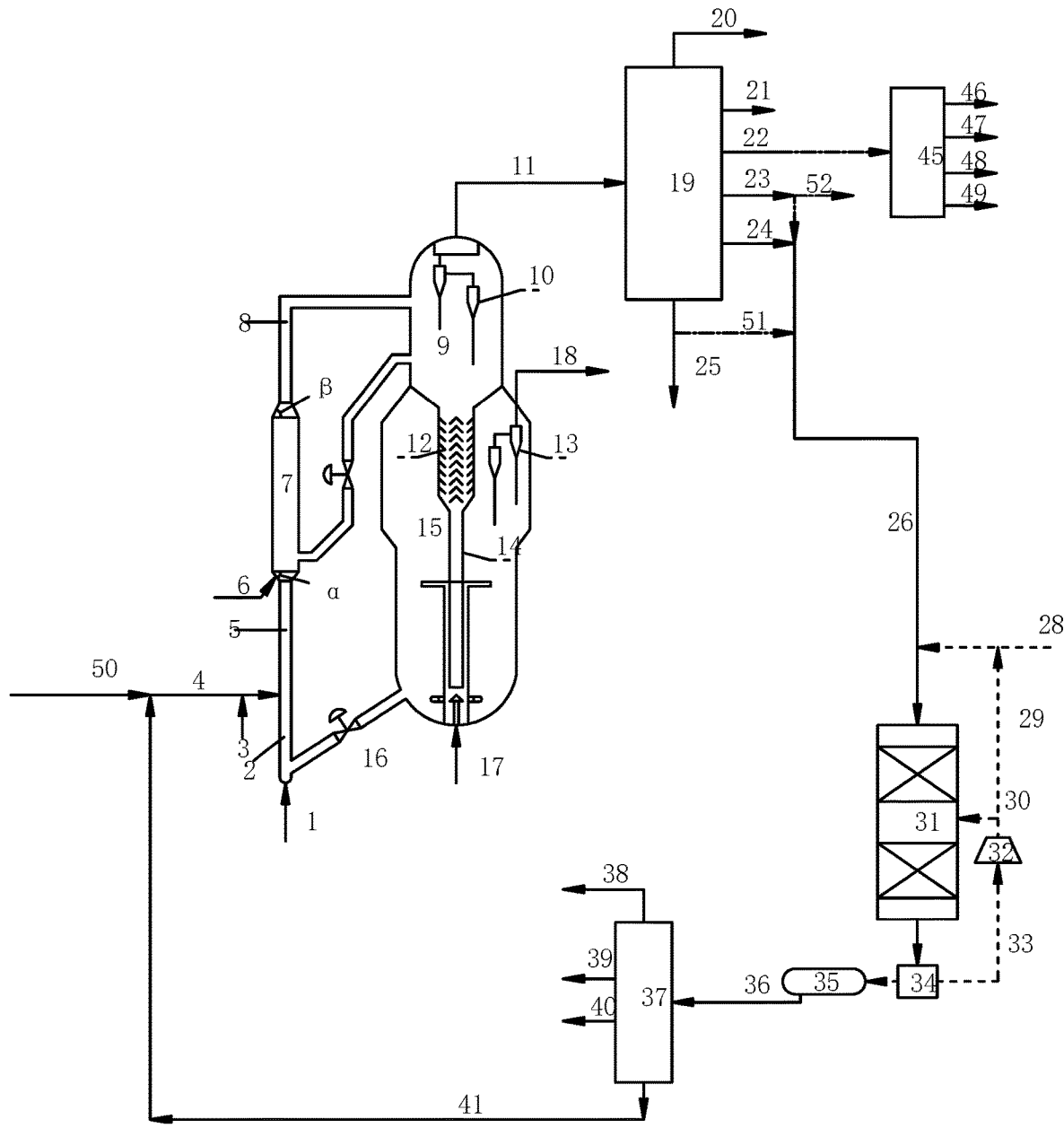
FIG. 1 shows a schematic flow diagram of a preferred embodiment of the process described herein.

| Description of the reference numerals | | |
|---|---|---|
| 1 Pipeline | 2 Pre-lifting section | 3 Pipeline |
| 4 Pipeline | 5 First reaction zone | 6 Pipeline |
| 7 Second reaction zone | 8 Outlet zone | 9 Disengager |
| 10 Cyclone separator | 11 Pipeline | 12 Stripper |
| 13 Cyclone separator | 14 Stand pipe for spent catalyst | |
| 15 Regenerator | 16 Sloped pipe for regenerated catalyst | |
| 17 Pipeline | 18 Pipeline | 19 Fractionation system |
| 20 Pipeline | 21 Pipeline | 22 Pipeline |
| 23 Pipeline | 24 Pipeline | 25 Pipeline |
| 26 Pipeline | 27 Pipeline | 28 Pipeline |
| 29 Pipeline | 30 Pipeline | 31 Hydrogenation unit |
| 32 Cyclic compressor | 33 Pipeline | |
| 34 High-pressure separator | 35 Low-pressure separator | |
| 36 Pipeline | 37 Fractionation column of the hydrogenation unit | |
| 38 Pipeline | 39 Pipeline | 40 Pipeline |
| 41 Pipeline | 42 Aromatics extraction unit | |
| 43 Pipeline | 44 Pipeline | |
| 45 Extraction refining unit | | 46 Pipeline |
| 47 Pipeline | 48 Pipeline | 49 Pipeline |
| 50 Pipeline | 51 Pipeline | 52 Pipeline |

DETAILED DESCRIPTION OF THE INVENTION

The present application will be further described hereinafter in detail with reference to specific embodiments thereof and the accompanying drawings. It should be noted that the specific embodiments of the present application are provided for illustration purpose only, and are not intended to be limiting in any manner.

Any specific numerical value, including the endpoints of a numerical range, described in the context of the present application is not restricted to the exact value thereof, but should be interpreted to further encompass all values close to said exact value. Moreover, regarding any numerical range described herein, arbitrary combinations can be made between the endpoints of the range, between each endpoint and any specific value within the range, or between any two specific values within the range, to provide one or more new numerical range(s), where said new numerical range(s) should also be deemed to have been specifically described in the present application.

Unless otherwise stated, the terms used herein have the same meaning as commonly understood by those skilled in the art; and if the terms are defined herein and their definitions are different from the ordinary understanding in the art, the definition provided herein shall prevail.

In the context of the present application, in addition to those matters explicitly stated, any matter or matters not mentioned are considered to be the same as those known in the art without any change. Moreover, any of the embodiments described herein can be freely combined with another one or more embodiments described herein, and the technical solutions or ideas thus obtained are considered as part of the original disclosure or original description of the present application, and should not be considered to be a new matter that has not been disclosed or anticipated herein, unless it is clear to those skilled in the art that such a combination is obviously unreasonable.

In this context, the terms "naphthene(s) having two or more rings" and "polycyclic naphthene(s)" are used interchangeably herein to refer to naphthene(s) having two or more carbocyclic rings.

In this context, the terms "aromatic(s) having two or more rings" and "polycyclic aromatic(s)" are used interchangeably herein to refer to aromatic compounds having two or more aromatic rings.

In this context, the term "water-to-oil ratio" refers to the mass ratio of atomizing steam to the feedstock oil.

All of the patent and non-patent documents cited herein, including but not limited to textbooks and journal articles, are hereby incorporated by reference in their entirety.

As described above, the present application provides a catalytic cracking process comprising the steps of:

a) providing a catalytic cracking feedstock oil having a polycyclic naphthene content of greater than about 25 wt %, based on the weight of the catalytic cracking feedstock oil;

b) contacting the catalytic cracking feedstock oil with a catalytic cracking catalyst in a catalytic cracking reactor, and subjecting the mixture to a first catalytic cracking reaction and a second catalytic cracking reaction sequentially under different reaction conditions to obtain a catalytic cracking product;

c) separating the resulting catalytic cracking product to obtain a liquefied gas fraction comprising isobutane and a gasoline fraction comprising light aromatics; and d) optionally, recovering isobutane from the liquefied gas fraction and/or recovering light aromatics from the gasoline fraction.

In certain preferred embodiments, the catalytic cracking feedstock oil has a polycyclic naphthene content of greater than about 40 wt %, the higher content the better.

In certain preferred embodiments, the separation in the step c) also produces a light cycle oil fraction, a heavy cycle oil fraction, and optionally a slurry oil, and the process further comprises the steps of:

e) subjecting at least a portion of the light cycle oil fraction, the heavy cycle oil fraction, and the optional slurry oil obtained in the step c) to a hydrotreatment to obtain a hydrogenated tail oil; and f) recycling at least a portion of the resulting hydrogenated tail oil to the catalytic cracking reactor.

In such preferred embodiments, said hydrotreatment in step e) is used to produce a hydrogenated tail oil (also referred to as hydrogenated distillate oil) rich in polycyclic naphthenes. Preferably, the hydrotreatment can be carried out under the following conditions: a hydrogen partial pressure between about 6.0 MPa and about 30.0 MPa, preferably between about 8 MPa and about 20 MPa, a reaction temperature between about 300° C. and about 450° C., preferably between about 330° C. and about 430° C., a liquid hourly space velocity (LHSV) between about 0.1 h$^{-1}$ and about 10.0 h$^{-1}$, preferably between about 0.2 h$^{-1}$ and about 5 h$^{-1}$, and a hydrogen-to-oil ratio by volume between about 300 Nm$^3$/m$^3$ and about 3000 Nm$^3$/m$^3$, preferably between about 500 Nm$^3$/m$^3$ and about 2500 Nm$^3$/m$^3$. For example, the hydrotreatment can be carried out under the following conditions: a hydrogen partial pressure between about 8 MPa and about 20 MPa, a reaction temperature between about 330° C. and about 430° C., a liquid hourly space velocity between about 0.2 h$^{-1}$ and about 5 h$^{-1}$, and a hydrogen-to-oil ratio by volume between about 500 Nm$^3$/m$^3$ and about 2500 Nm$^3$/m$^3$.

Further preferably, the hydrotreatment may be carried out in the presence of a hydrotreating catalyst that may comprise a hydrotreating active component that may be selected from the group consisting of Group VIB non-noble metals, Group VIII non-noble metals, and combinations thereof, and a support that may be selected from the group consisting of alumina, silica, amorphous silica-alumina, and combinations thereof. Preferably, the Group VIII non-noble metal is present in an amount of from about 1 wt % to about 99 wt %, preferably from about 1 wt % to about 60 wt %, calculated as oxide and based on the weight of the hydrotreating catalyst; and/or the Group VIB non-noble metal is present in an amount of about 1 wt % to about 99 wt %, preferably about 1 wt % to about 70 wt %. Preferably, the Group VIII non-noble metal is cobalt and/or nickel, and the Group VIB non-noble metal is molybdenum and/or tungsten. The hydrotreating catalyst shows excellent performance in the hydrogenation saturation of aromatics, and can be used to effectively convert the aromatics in the light cycle oil fraction, the heavy cycle oil fraction and the slurry oil into naphthenes through hydrogenation saturation, so as to provide a feedstock for the catalytic cracking process according to the present application.

In such preferred embodiments, the slurry oil produced by the catalytic cracking reaction may be optionally sent to a slurry oil filtration system, then sent to a hydrogenation unit for hydrogenation saturation, and at least partially recycled to the catalytic cracking reactor, or alternatively the slurry oil produced may be directly discharged from the device.

In certain preferred embodiments, said step a) further comprises subjecting an initial feedstock oil having a polycyclic naphthene content of no greater than about 25 wt % to a pretreatment to obtain the catalytic cracking feedstock oil having a polycyclic naphthene content of greater than about 25 wt %, preferably greater than about 40 wt %.

For example, the initial feedstock oil having a polycyclic naphthene content of no greater than about 25 wt % may be a feedstock oil having a total polycyclic naphthene and polycyclic aromatic content of greater than about 25 wt %. In this case, the initial feedstock oil may be subjected to a hydrotreatment to convert the polycyclic aromatics into polycyclic naphthenes through hydrogenation saturation, so that a catalytic cracking feedstock oil having a polycyclic naphthene content of greater than about 25 wt % can be obtained.

Preferably, the hydrotreatment can be carried out under the following conditions: a hydrogen partial pressure between about 6.0 MPa and about 30.0 MPa, preferably between about 8 MPa and about 20 MPa, a reaction temperature between about 300° C. and about 450° C., preferably between about 330° C. and about 430° C., a liquid hourly space velocity between about 0.1 h$^{-1}$ and about 10.0 h$^{-1}$, preferably between about 0.2 h$^{-1}$ and about 5 h$^{-1}$, and a hydrogen-to-oil ratio by volume between about 300 Nm$^3$/m$^3$ and about 3000 Nm$^3$/m$^3$, preferably between about 500 Nm$^3$/m$^3$ and about 2500 Nm$^3$/m$^3$.

Further preferably, the hydrotreatment may be carried out in the presence of a hydrotreating catalyst that may comprise a hydrotreating active component that may be selected from the group consisting of Group VIB non-noble metals, Group VIII non-noble metals, and combinations thereof, and a support that may be selected from the group consisting of alumina, silica, amorphous silica-alumina, and combinations thereof. Preferably, the Group VIII non-noble metal is present in an amount of from about 1 wt % to about 99 wt %, preferably from about 1 wt % to about 60 wt %, calculated as oxide and based on the weight of the hydrotreating catalyst; and/or the Group VIB non-noble metal is present in an amount of about 1 wt % to about 99 wt %, preferably about 1 wt % to about 70 wt %. Preferably, the Group VIII non-noble metal is cobalt and/or nickel, and the Group VIB non-noble metal is molybdenum and/or tungsten.

Alternatively, an initial feedstock oil having a polycyclic naphthene content of no greater than about 25 wt % may be subjected to aromatics extraction, and then optionally to a hydrotreatment as described above. For example, the initial feedstock oil may be separated into a raffinate oil rich in polycyclic naphthenes and an extract oil rich in polycyclic aromatics by aromatics extraction; the extract oil may be optionally further subjected to hydrofining to saturate the polycyclic aromatics contained therein to form polycyclic naphthenes.

In such embodiments, the aromatics extraction may be performed in a manner well known to those skilled in the art. Preferably, the aromatics extraction may be carried out under the following conditions: a temperature of about 50° C. to about 70° C., a solvent-to-feedstock ratio by weight of about 0.5 to about 2, a solvent selected from the group consisting of furfural, dimethyl sulfoxide, dimethylformamide, monoethanolamine, ethylene glycol, and 1,2-propanediol, and combinations thereof.

The catalytic cracking feedstock oil suitable for use in the process described herein may be any feedstock oil having a polycyclic naphthene content of greater than about 25 wt %, preferably greater than about 40 wt %; the initial feedstock oil suitable for use in the process described herein can be any feedstock oil that may have a polycyclic naphthene content of greater than about 25 wt %, preferably greater than about 40 wt %, after said pretreatment. For example, the catalytic cracking feedstock oil or the initial feedstock oil may be selected from the group consisting of deep-hydrogenated light cycle oil, coker gas oil (CGO) from delayed coker, catalytic cracking light cycle oil (LCO), catalytic cracking heavy cycle oil (HCO), FCC gas oil (FGO), slurry oil, hydrocracked diesel oil, residuum hydrocracked diesel oil, wax oil hydrocracked diesel oil, biodiesel, diesel fraction of shale oil, diesel fraction from coal liquefaction, atmospheric overhead oil, distillate oil extracted from atmospheric column, straight-run vacuum gas oil, hydrogenated wax oil, coker gas oil, deasphalted oil (DAO), extract oil, raffinate oil, atmospheric residuum, vacuum residuum, hydrogenated tail oils obtained from the above feedstock oils by hydrogenation, and combinations thereof.

In the process described herein, the first and second catalytic cracking reactions may be carried out in a manner well known to those skilled in the art under different reaction conditions, wherein the first catalytic cracking reaction comprises primarily a cracking reaction and the second catalytic cracking reaction comprises primarily a selective hydrogen transfer reaction, an isomerization reaction, and an aromatization reaction. Preferably, the first catalytic cracking reaction may be carried out under the following conditions: a reaction temperature between about 520° C. and about 620° C., preferably between about 530° C. and 600° C.; a reaction time between about 0.5 seconds and about 3.0 seconds, preferably between about 0.8 seconds and about 2.0 seconds; a catalyst-to-oil ratio by weight between about 3:1 and about 15:1, preferably between about 4:1 and about 12:1; a water-to-oil ratio between about 0.03:1 and about 0.3:1, preferably between about 0.05:1 and about 0.3:1; a pressure between 130 kPa and 450 kPa; and/or, the second catalytic cracking reaction may be carried out under the following conditions: a reaction temperature between about 480° C. and about 600° C., preferably between about 500° C. and about 550° C., or between about 420° C. and about 530° C., preferably between about 460° C. and about 510° C.; a reaction time between about 2 seconds and about 30 seconds, preferably between about 3 seconds and about 15 seconds; a catalyst-to-oil ratio by weight between about 3:1 and about 18:1, preferably between about 4:1 and about 15:1; a water-to-oil ratio between about 0.03:1 and about 0.3:1, preferably between about 0.05:1 and about 0.3:1; and a pressure between 130 kPa and 450 kPa.

The catalytic cracking reactor suitable for use in the process described herein may be any catalytic cracking reactor known to those skilled in the art, provided that the first and second catalytic cracking reactions can be carried out therein under different reaction conditions. For example, the catalytic cracking reactor may be a conventional riser reactor, an equal-linear-velocity riser reactor, a dual diameter riser reactor, a fluidized bed reactor, or a composite reactor composed of a conventional riser and a fluidized bed, and preferably a dual diameter riser reactor.

In certain preferred embodiments, the catalytic cracking reactor is a dual diameter riser reactor, which comprises a pre-lifting section, a first reaction zone, a second reaction zone and an outlet zone disposed sequentially from bottom to top in the vertical direction that are coaxial and in fluid communication, in which a horizontal pipe connecting to a disengager is provided at the end of the outlet zone, the inner diameter of the first reaction zone is smaller than that of the second reaction zone, the inner diameter of the second reaction zone is larger than that of the outlet zone, the catalytic cracking catalyst is fed into the pre-lifting section, the catalytic cracking feedstock oil is fed into the lower part of the first reaction zone, the first catalytic cracking reaction is carried out in the first reaction zone, and the second catalytic cracking reaction is carried out in the second reaction zone.

In certain particularly preferred embodiments, the dual diameter riser reactor has a total height (including the pre-lifting section, the first reaction zone, the second reaction zone, and the outlet zone) of from about 10 meters to about 60 meters. The pre-lifting section may have the same diameter as that in a conventional riser reactor, which is typically about 0.2 meters to about 5 meters, and may have a height of about 5% to about 20% relative to the total height of the reactor. The first reaction zone has a configuration similar to a conventional riser reactor, and may have a diameter equal to or slightly larger than that of the pre-lifting section, the ratio of the diameter of the first reaction zone to the diameter of the pre-lifting section is about 1:1 to about 2:1, and the height of the first reaction zone is about 10% to about 30% relative to the total height of the reactor. After the feedstock oil and the catalyst are mixed in this zone, a primarily cracking reaction occurs at a higher reaction temperature and a higher catalyst-to-oil ratio for a shorter reaction time (typically about 0.5 seconds to about 3.0 seconds). The second reaction zone has a diameter larger than that of the first reaction zone, with the ratio of the diameter of the second reaction zone to the diameter of the first reaction zone being about 1.5:1 to about 5.0:1, and has a height of about 10% to about 60% relative to the total height of the reactor, and plays a role to reduce the flow rate of the oil gas and the catalyst and reduce the reaction temperature, so that they are primarily subjected to selective hydrogen transfer reaction, isomerization reaction and aromatization reaction. The reaction time of the oil gas in the reaction zone may be relatively long, for example, be about 2 seconds to 30 seconds. The ratio of the diameter of the outlet zone to the diameter of the first reaction zone is from about 0.8:1 to about 1.5:1, and the height of the outlet zone is about 0% to about 50% relative to the total height of the reactor. The joint part between the first reaction zone and the second reaction zone has a circular truncated cone shape, with the vertex angle α of its isosceles trapezoid longitudinal section being about 30 degrees to about 80 degrees; and the joint part between the second reaction zone and the outlet zone has a circular truncated cone shape, with the vertex angle β of its isosceles trapezoid longitudinal section being about 45 degrees to about 85 degrees. The method for reducing the reaction temperature of the second reaction zone may comprise injecting a quench medium through the joint between this zone and the first reaction zone, and/or removing a part of heat by providing a cooler in this zone, thereby achieving the purposes of inhibiting the secondary cracking reaction, and enhancing the isomerization reaction and the hydrogen transfer reaction. The quench medium may be selected from the group consisting of a chilling agent, a cooled regenerated catalyst, and a cooled semi-regenerated catalyst, and combinations thereof. The chilling agent may be selected from the group consisting of liquefied gas, crude gasoline, stabilized gasoline, light cycle oil fraction, heavy cycle oil fraction, water, and combinations thereof; the cooled regenerated catalyst and the cooled semi-regenerated catalyst can be obtained by subjecting the spent catalyst to a two-stage regeneration and an one-stage regeneration, respectively, and then cooling. The regenerated catalyst generally has a carbon content of about 0.1 wt % or less, preferably about 0.05 wt % or less, and the semi-regenerated catalyst generally has a carbon content of about 0.1 wt % to about 0.9 wt %, preferably about 0.15 wt % to about 0.7 wt %. If a cooler is provided, it may have a height of about 50% to about 90% relative to the height of the second reaction zone.

In a further preferred embodiment, the joint region between the first reaction zone and the second reaction zone is provided with at least one quench medium inlet for injecting the quench medium; and/or the second reaction zone is provided with a cooler, with the height of the cooler being about 50% to about 90% relative to the height of the second reaction zone.

In a still further preferred embodiment, the quench medium is selected from the group consisting of a chilling agent, a cooled regenerated catalyst, a cooled semi-regenerated catalyst, a fresh catalyst, and combinations thereof; and the chilling agent is selected from the group consisting of liquefied gases, crude gasolines, stabilized gasolines, light cycle oils, heavy cycle oils, water, and combinations thereof.

Suitable catalytic cracking catalysts for use in the process described herein may be those well known to those skilled in the art. For example, the catalytic cracking catalyst may comprise a cracking active component and a support; the cracking active component may comprise about 0-100 wt %, preferably about 10-90 wt %, more preferably about 20-40 wt % of FAU-type zeolite and about 0-100 wt %, preferably about 10-90 wt %, more preferably about 60-80 wt % of pentasil zeolite, wherein the total amount of the FAU-type zeolite and the pentasil zeolite is 100 wt %, based on the weight of the cracking active component on a dry basis; the FAU-type zeolite is preferably selected from the group consisting of Y-type zeolites, HY-type zeolites, ultrastable Y-type zeolites, and combinations thereof, the pentasil zeolite is preferably selected from the group consisting of ZSM-5 zeolites, high-silica zeolites, ferrierites, and combinations thereof, and the pentasil zeolite may optionally contain rare earth and/or phosphorus.

In certain embodiments of the process described herein, the spent catalyst generated from the catalytic cracking catalyst after reaction may be sent to a regenerator for regeneration via coke burning, and the regenerated catalyst resulted from the regeneration may be recycled to the catalytic cracking reactor as the catalytic cracking catalyst.

Figure 2:
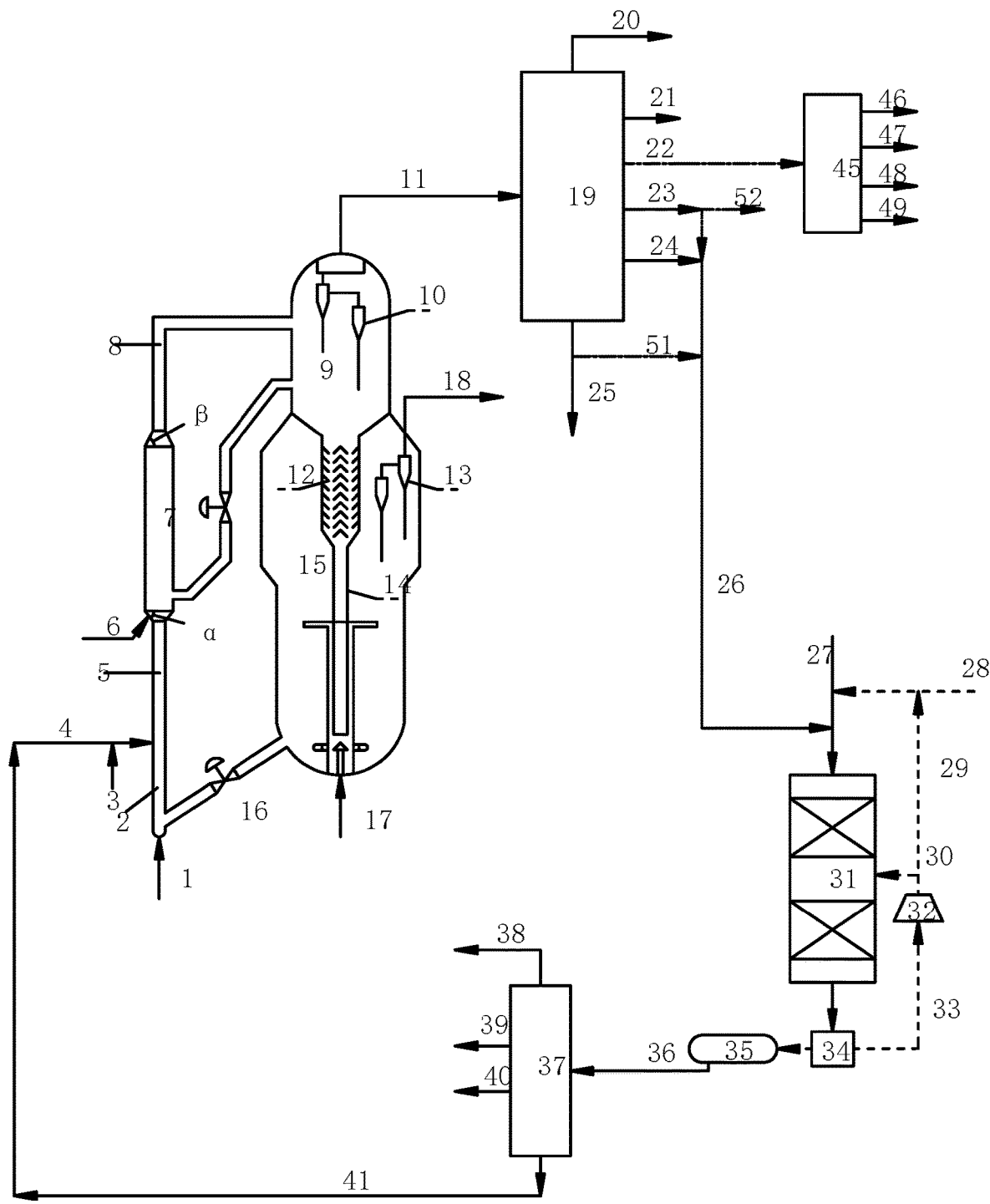
FIG. 2 shows a schematic flow diagram of another preferred embodiment of the process described herein.
Figure 3:
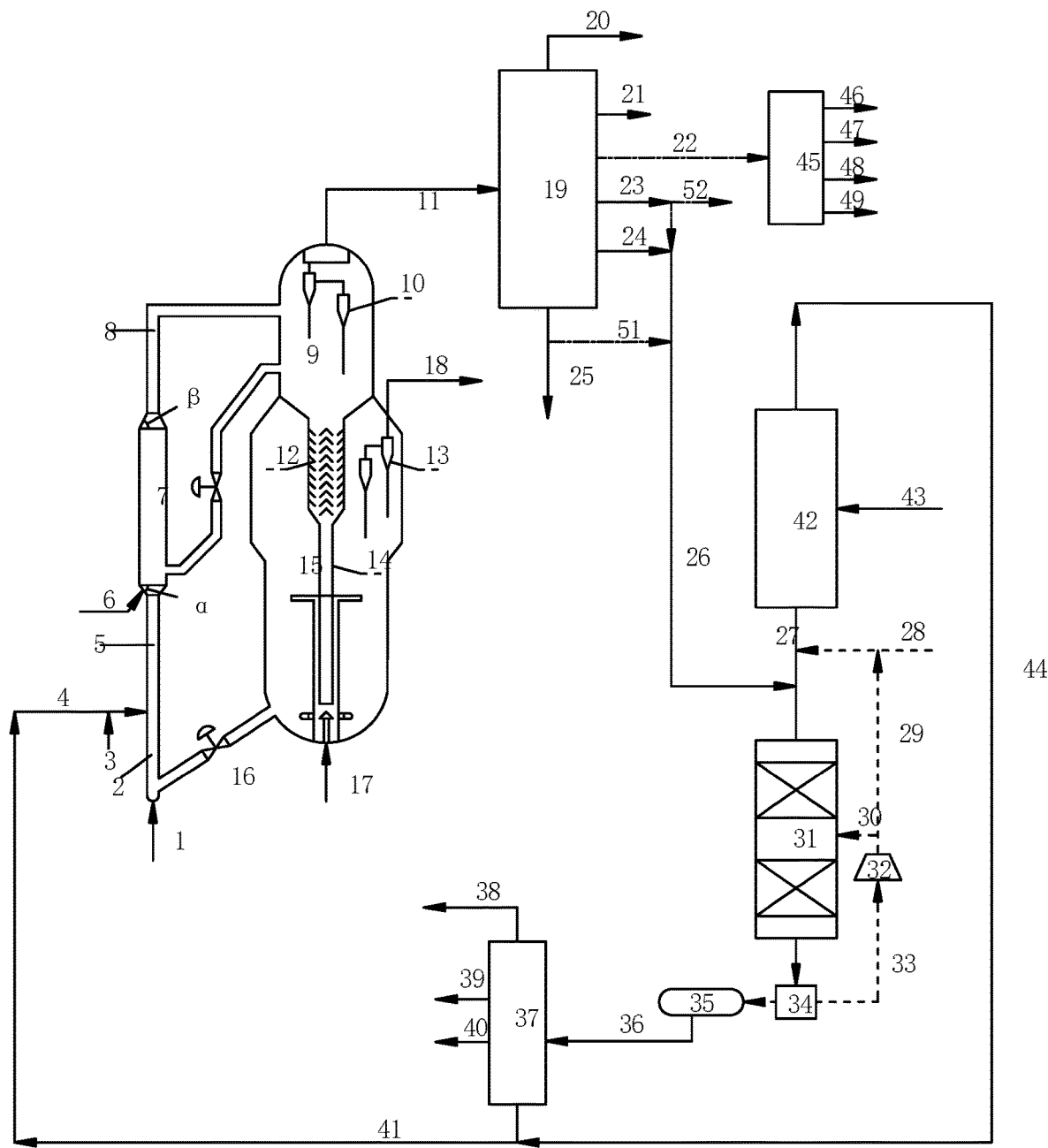
FIG. 3 shows a schematic flow diagram of still another preferred embodiment of the process described herein.

In order to enhance the hydrogen transfer reaction and the isomerization reaction in the second reaction zone, as shown in FIG. 1-3, a portion of the spent catalyst in the disengager may optionally be sent to the second reaction zone as a quench medium to promote the production of isoparaffins and light aromatics.

In certain preferred embodiments of the process described herein, light aromatics (BTX) may be recovered from the gasoline fraction by extraction refining in step d). The extraction refining may be carried out in a manner well known to those skilled in the art. For example, the extraction refining may be carried out under the following conditions: an extraction solvent selected from the group consisting of sulfolane, dimethyl sulfoxide, N-formylmorpholine, tetraethylene glycol, triethylene glycol, N-methylpyridinone, and combinations thereof, a temperature of from about 50° C. to about 110° C. and a weight ratio of extraction solvent to gasoline fraction between about 2 and about 6.

In a particularly preferred embodiment, the catalytic cracking process described herein comprises the steps of:

a) providing a catalytic cracking feedstock oil having a polycyclic naphthene content of greater than about 25 wt %, based on the weight of the catalytic cracking feedstock oil;

b) sending the catalytic cracking feedstock oil into a catalytic cracking reactor to contact with a catalytic cracking catalyst, and subjecting the mixture to a first catalytic cracking reaction and a second catalytic cracking reaction sequentially under different reaction conditions to obtain a catalytic cracking product and a spent catalyst;

c) separating the catalytic cracking product to obtain a dry gas, a liquefied gas fraction, a gasoline fraction, a light cycle oil fraction, a heavy cycle oil fraction and optionally a slurry oil;

d) optionally, subjecting the gasoline fraction obtained in the step c) to extraction refining to obtain light aromatics (such as benzene, toluene and xylene), and/or separating the liquefied gas fraction obtained in the step c) to obtain propylene and isobutane products;

e) optionally, sending the light cycle oil fraction, the heavy cycle oil fraction and the optional slurry oil, preferably after filtration, obtained in the step c) to a hydrogenation unit to contact with a hydrotreating catalyst and to carry out a hydrotreatment; and f) optionally, feeding the resulting hydrogenated tail oil into the catalytic cracking reactor as the catalytic cracking feedstock oil.

In a kind of preferred embodiments of the process described herein, a preheated catalytic cracking feedstock oil is fed into a dual diameter riser reactor, through the lower part of the first reaction zone of the reactor, to contact with a catalyst and primarily conduct a cracking reaction; the mixture of oil gas and catalyst generated after the reaction is lifted up to the lower part of the second reaction zone of the reactor, optionally contacted with a cooled catalyst, to primarily conduct a hydrogen transfer reaction and an isomerization reaction, and the reaction effluent is sent to a disengager for separation to obtain a reaction oil gas (namely a catalytic cracking product) and a spent catalyst. The reaction oil gas is then separated to obtain reaction products including a dry gas, a liquefied gas fraction, a gasoline fraction, a light cycle oil fraction, a heavy cycle oil fraction and a slurry oil. Optionally, the light cycle oil fraction, the heavy cycle oil fraction and/or the slurry oil, and optionally a distillate oil from other processing units are sent to a hydrogenation unit to conduct a hydrotreatment in the presence of a hydrotreating catalyst, and the resulting hydrogenated tail oil is recycled to the riser reactor. The spent catalyst is recycled to the riser reactor after being stripped and regenerated.

Such kind of preferred embodiments of the present application will be further described with reference to FIG. 1, but the present invention is not limited thereto.

FIG. 1 schematically illustrates an exemplary process for producing isobutane and a gasoline rich in aromatics using a dual diameter riser reactor, in which the shape, size, etc. of the equipment and pipelines are not limited by the drawings, but should be determined in view of particular circumstances.

As shown in FIG. 1, a pre-lifting steam is injected into the pre-lifting section 2 of the dual diameter riser reactor through a pipeline 1, and a hot regenerated catalyst is sent to the pre-lifting section 2 through a sloped pipe for regenerated catalyst 16 and is lifted by the pre-lifting steam. A catalytic cracking feedstock oil (e.g., a distillate oil from other processing units) from a pipeline 50 is combined with a hydrogenated tail oil from a pipeline 41, sent to the pre-lifting section 2 via a pipeline 4 along with an atomized steam from a pipeline 3, mixed with the hot regenerated catalyst and passed into the first reaction zone 5 to conduct a first catalytic cracking reaction therein. The reaction stream is mixed with a chilling agent from a pipeline 6 and/or a cooled catalyst (not shown in the drawings) and passed into the second reaction zone 7 for a second catalytic cracking reaction. The reaction effluent is passed into an outlet zone 8, in which the linear velocity of the stream can be increased, so that the reaction effluent is rapidly passed into a disengager 9 and a cyclone separator 10 of a gas-solid separation system for separation. The separated spent catalyst is passed into a stripper 12, then into a stand pipe for spent catalyst 14 after being stripped, and is passed into a regenerator 15 by the lifting of air from a pipeline 17 for regeneration via coke burning therein. The flue gas resulted from the separation in a cyclone separator 13 is discharged from the regenerator through a pipeline 18, and the hot regenerated catalyst is recycled to the bottom of the riser reactor through the sloped pipe for regenerated catalyst 16 for reuse. Optionally, a portion of the spent catalyst in the disengager may be sent to the second reaction zone 7 as a quench medium. The separated reaction oil gas is sent to a fractionation system 19 through a pipeline 11, and the dry gas obtained by fractionation is withdrawn through a pipeline 20; the liquefied gas fraction is sent to a subsequent processing unit (not shown in the drawings) via a pipeline 21 for the separation of isobutane; the gasoline fraction is preferably sent to an extraction refining unit 45 via a pipeline 22, and the resulting benzene, toluene, xylene and raffinate are discharged from a pipeline 46, a pipeline 47, a pipeline 48 and a pipeline 49, respectively; the light cycle oil fraction is withdrawn via a pipeline 23 and optionally discharged from the catalytic cracking device via a pipeline 52 or sent to a hydrogenation unit 31 via a pipeline 26; the heavy cycle oil fraction is withdrawn via a pipeline 24 and optionally sent to the hydrogenation unit 31 via the pipeline 26; the slurry oil is optionally discharged from the device via a pipeline 25 or sent to the hydrogenation unit 31 via a pipeline 51 and the pipeline 26. The stream from the pipeline 26 and the hydrogen from a pipeline 28 are passed into the hydrogenation unit 31 for hydrotreatment, the hydrogenation product is sent to a high-pressure separator 34 and a low-pressure separator 35 for separation, the liquid product is sent to a fractionation column 37 of the hydrogenation unit for separation via a pipeline 36 to obtain a gas, a hydrogenated gasoline, a hydrogenated light cycle oil and a hydrogenated tail oil, which are discharged from a pipeline 38, a pipeline 39, a pipeline 40 and a pipeline 41, respectively. Hydrogen is sent to a hydrogen cyclic compressor 32 via a pipeline 33 for compression and then recycled to the hydrogenation unit 31 via a pipeline 30, a pipeline 29 and a pipeline 28. The hydrogenated tail oil is sent via the pipeline 41, the pipeline 4, along with the atomizing steam from the pipeline 3, to the pre-lifting section 2.

In another kind of preferred embodiments of the process described herein, the initial feedstock oil is processed through a hydrogenation unit to obtain a hydrogenated tail oil, which is then fed to the dual diameter riser reactor as the catalytic cracking feedstock oil. Preheated hydrogenated tail oil is sent to the lower part of the first reaction zone of the reactor to contact with a catalyst and primarily conduct a cracking reaction, the mixture of oil gas and catalyst generated after the reaction is lifted up to the lower part of the second reaction zone of the reactor, optionally contacted with the cooled catalyst, to primarily conduct a hydrogen transfer reaction and an isomerization reaction, the reaction effluent is sent to a disengager for separation to obtain a reaction oil gas and a spent catalyst. The reaction oil gas is then separated to obtain reaction products including a dry gas, a liquefied gas fraction, a gasoline fraction, a light cycle oil fraction, a heavy cycle oil fraction and a slurry oil. Optionally, the light cycle oil fraction, the heavy cycle oil fraction and/or the slurry oil, and optionally a distillate oil from other processing units are sent to a hydrogenation unit for hydrotreatment in the presence of a hydrotreating catalyst, and the resulting hydrogenated tail oil is recycled to the riser reactor. The spent catalyst is recycled to the riser reactor after being stripped and regenerated.

Such kind of preferred embodiments of the present application will be further described with reference to FIG. 2, but the present invention is not limited thereto.

FIG. 2 schematically illustrates another exemplary process for producing isobutane and a gasoline rich in aromatics using a dual diameter riser reactor, in which the shape, size, etc. of the equipment and pipelines are not limited by the drawings, but should be determined in view of particular circumstances.

As shown in FIG. 2, a pre-lifting steam is injected into the pre-lifting section 2 of the dual diameter riser reactor through a pipeline 1, and a hot regenerated catalyst is sent to the pre-lifting section 2 through a sloped pipe for regenerated catalyst 16 and is lifted by the pre-lifting steam. An initial feedstock oil (e.g., a distillate oil from other processing units) from a pipeline 27 is passed into a hydrogenation unit 31 for hydrotreatment along with the hydrogen from a pipeline 28 and optionally the stream from a pipeline 26, the hydrogenated product is sent to a high-pressure separator 34 and a low-pressure separator 35 for separation, the liquid product is sent to a fractionation column 37 of the hydrogenation unit for separation via a pipeline 36 to obtain a gas, a hydrogenated gasoline, a hydrogenated light cycle oil, and a hydrogenated tail oil, which are discharged from a pipeline 38, a pipeline 39, a pipeline 40, and a pipeline 41, respectively. Hydrogen is sent to a hydrogen cyclic compressor 32 via a pipeline 33 for compression and then recycled to the hydrogenation unit 31 via a pipeline 30, a pipeline 29 and a pipeline 28. The hydrogenated tail oil is sent to the pre-lifting section 2 as the catalytic cracking feedstock oil through a pipeline 41 and a pipeline 4 along with an atomized steam from a pipeline 3, mixed with a hot regenerated catalyst and then is passed into the first reaction zone 5 to conduct a first catalytic cracking reaction therein. The reaction stream is mixed with a chilling agent from a pipeline 6 and/or a cooled catalyst (not shown in the drawings) and passed into the second reaction zone 7 for a second catalytic cracking reaction. The reaction effluent is passed into an outlet zone 8, in which the linear velocity of the stream can be increased, so that the reaction effluent is rapidly passed into a disengager 9 and a cyclone separator 10 of a gas-solid separation system for separation. The separated spent catalyst is passed into a stripper 12, then into a stand pipe for spent catalyst 14 after being stripped, and is passed into a regenerator 15 by the lifting of air from a pipeline 17 for regeneration via coke burning therein. The flue gas resulted from the separation in a cyclone separator 13 is discharged from the regenerator through a pipeline 18, and the hot regenerated catalyst is recycled to the bottom of the riser reactor through the sloped pipe for regenerated catalyst 16 for reuse. Optionally, a portion of the spent catalyst in the disengager may be sent to the second reaction zone 7 as a quench medium. The separated reaction oil gas is sent to a fractionation system 19 through a pipeline 11, and the dry gas obtained by fractionation is withdrawn through a pipeline 20; the liquefied gas fraction is sent to a subsequent processing unit (not shown in the drawings) via a pipeline 21 for the separation of isobutane; the gasoline fraction is preferably sent to an extraction refining unit 45 via a pipeline 22, and the resulting benzene, toluene, xylene and raffinate are discharged from a pipeline 46, a pipeline 47, a pipeline 48 and a pipeline 49, respectively; the light cycle oil fraction is withdrawn via a pipeline 23 and optionally discharged from the catalytic cracking device via a pipeline 52 or sent to a hydrogenation unit 31 via a pipeline 26; the heavy cycle oil fraction is withdrawn via a pipeline 24 and optionally sent to the hydrogenation unit 31 via the pipeline 26; the slurry oil is optionally discharged from the device via a pipeline 25 or sent to the hydrogenation unit 31 via a pipeline 51 and the pipeline 26. The stream from the pipeline 26 is passed into the hydrogenation unit 31 for hydrotreatment, along with the initial feedstock oil from the pipeline 27, and the hydrogen from the pipeline 28.

In another kind of preferred embodiments of the process described herein, the initial feedstock oil is processed through an aromatics extraction unit to produce an extract oil rich in polycyclic aromatics and a raffinate oil rich in polycyclic naphthenes. The extract oil is processed through a hydrogenation unit to obtain a hydrogenated tail oil, and the hydrogenated tail oil and the raffinate oil are combined and fed to a dual diameter riser reactor as the catalytic cracking feedstock oil. A preheated catalytic cracking feedstock oil is sent to the lower part of the first reaction zone of the reactor to contact with a catalyst and primarily conduct a cracking reaction, the mixture of oil gas and catalyst generated after the reaction is lifted up to the lower part of the second reaction zone of the reactor, optionally contacted with a cooled catalyst, to primarily conduct a hydrogen transfer reaction and an isomerization reaction, the reaction effluent is sent to a disengager for separation to obtain a reaction oil gas and a spent catalyst. The reaction oil gas is then separated to obtain reaction products including a dry gas, a liquefied gas fraction, a gasoline fraction, a light cycle oil fraction, a heavy cycle oil fraction and a slurry oil. Optionally, the light cycle oil fraction, the heavy cycle oil fraction and/or the slurry oil, and optionally a distillate oil from other processing units are sent to a hydrogenation unit for hydrotreatment in the presence of a hydrotreating catalyst, and the resulting hydrogenated tail oil is recycled to the riser reactor. The spent catalyst is recycled to the riser reactor after being stripped and regenerated.

Such kind of preferred embodiments of the present application will be further described with reference to FIG. 3, but the present invention is not limited thereto.

FIG. 3 schematically illustrates another exemplary process for producing isobutane and a gasoline rich in aromatics using a dual diameter riser reactor, in which the shape, size, etc. of the equipment and pipelines are not limited by the drawings, but should be determined in view of particular circumstances.

As shown in FIG. 3, a pre-lifting steam is injected into the pre-lifting section 2 of the dual diameter riser reactor through a pipeline 1, and a hot regenerated catalyst is sent to the pre-lifting section 2 through a sloped pipe for regenerated catalyst 16 and is lifted by the pre-lifting steam. An initial feedstock oil (e.g., a distillate oil from other processing units) from a pipeline 43 is passed into an aromatics extraction unit 42 and is extracted to produce an extract oil rich in polycyclic aromatics and a raffinate oil rich in polycyclic naphthenes. The extract oil is passed into a hydrogenation unit 31 for hydrotreatment via a pipeline 27, along with the hydrogen from a pipeline 28 and optionally a stream from a pipeline 26, the hydrogenation product is sent to a high-pressure separator 34 and a low-pressure separator 35 for separation, the liquid product is sent to a fractionation column 37 of the hydrogenation unit for separation to obtain a gas, a hydrogenated gasoline, a hydrogenated light cycle oil and a hydrogenated tail oil, which are discharged through the pipeline 38, the pipeline 39, the pipeline 40 and the pipeline 41, respectively. Hydrogen is sent to a hydrogen cyclic compressor 32 via a pipeline 33 for compression and then recycled to the hydrogenation unit 31 via a pipeline 30, a pipeline 29 and a pipeline 28. The hydrogenated tail oil and the raffinate oil from a pipeline 44 are combined and fed into the pre-lifting section 2 through a pipeline 41, a pipeline 4 as the catalytic cracking feedstock oil, along with an atomized steam from a pipeline 3, mixed with a hot regenerated catalyst and then passed into the first reaction zone 5 to conduct a first catalytic cracking reaction therein. The reaction stream is mixed with a chilling agent from a pipeline 6 and/or a cooled catalyst (not shown in the drawings) and passed into the second reaction zone 7 for a second catalytic cracking reaction. The reaction effluent is passed into an outlet zone 8, in which the linear velocity of the stream can be increased, so that the reaction effluent is rapidly passed into a disengager 9 and a cyclone separator 10 of a gas-solid separation system for separation. The separated spent catalyst is passed into a stripper 12, then into a stand pipe for spent catalyst 14 after being stripped, and is passed into a regenerator 15 by the lifting of air from a pipeline 17 for regeneration via coke burning therein. The flue gas resulted from the separation in a cyclone separator 13 is discharged from the regenerator through a pipeline 18, and the hot regenerated catalyst is recycled to the bottom of the riser reactor through the sloped pipe for regenerated catalyst 16 for reuse. Optionally, a portion of the spent catalyst in the disengager may be sent to the second reaction zone 7 as a quench medium. The separated reaction oil gas is sent to a fractionation system 19 through a pipeline 11, and the dry gas obtained by fractionation is withdrawn through a pipeline 20; the liquefied gas fraction is sent to a subsequent processing unit (not shown in the drawings) via a pipeline 21 for the separation of isobutane; the gasoline fraction is preferably sent to an extraction refining unit 45 via a pipeline 22, and the resulting benzene, toluene, xylene and raffinate are discharged from a pipeline 46, a pipeline 47, a pipeline 48 and a pipeline 49, respectively; the light cycle oil fraction is withdrawn via a pipeline 23 and optionally discharged from the catalytic cracking device via a pipeline 52 or sent to a hydrogenation unit 31 via a pipeline 26; the heavy cycle oil fraction is withdrawn via a pipeline 24 and optionally sent to the hydrogenation unit 31 via the pipeline 26; the slurry oil is optionally discharged from the device via a pipeline 25 or sent to the hydrogenation unit 31 via the pipeline 51 and the pipeline 26. The stream from the pipeline 26 is passed into the hydrogenation unit 31 for hydrotreatment, along with the extract oil from the pipeline 27 and the hydrogen from the pipeline 28.

In a preferred embodiment, the present application provides the following technical solutions:

A1. A catalytic cracking process for producing isobutane and light aromatics in high yield, comprising the following steps:

(1) feeding a catalytic cracking feedstock oil into a catalytic cracking reactor to contact with a catalytic cracking catalyst, and subjecting the mixture to a first catalytic cracking reaction and a second catalytic cracking reaction sequentially under different reaction conditions to obtain a catalytic cracking product and a spent catalyst; wherein the catalytic cracking feedstock oil has a polycyclic naphthene content of greater than about 25 wt %;

(2) separating the resulting catalytic cracking product to obtain a dry gas, a liquefied gas, a gasoline, a light cycle oil fraction, a heavy cycle oil fraction and optionally a slurry oil;

(3) optionally, sending the light cycle oil fraction, the heavy cycle oil fraction and the slurry oil obtained in the step (2) to a hydrogenation unit to contact with a hydrotreating catalyst and carry out a selective hydrotreatment to obtain a hydrogenated tail oil, and sending the hydrogenated tail oil to the catalytic cracking reactor as the catalytic cracking feedstock oil;

(4) optionally, subjecting the gasoline obtained in the step (2) to extraction refining to obtain light aromatics.

A2. The process of Item A1, wherein the catalytic cracking feedstock oil has a polycyclic naphthene content of greater than about 40 wt %.

A3. The process of Item A1, wherein the catalytic cracking feedstock oil is at least one primary processing distillate oil and/or secondary processing feedstock selected from the group consisting of deep-hydrogenated light cycle oil, coker gas oil from delayed coker, catalytic cracking light cycle oil, catalytic cracking heavy cycle oil, FCC gas oil, slurry oil, hydrocracked diesel oil, residuum hydrocracked diesel oil, wax oil hydrocracked diesel oil, biodiesel, diesel fraction of shale oil, diesel fraction from coal liquefaction, atmospheric overhead oil, distillate oil extracted from atmospheric column, straight-run vacuum gas oil, hydrogenated wax oil, coker gas oil, deasphalted oil, extract oil, raffinate oil, atmospheric residuum and vacuum residuum, and/or a hydrogenated tail oil obtained from the at least one primary processing distillate oil and/or secondary processing feedstock by hydrogenation.

A4. The process of Item A3, wherein, in case where the secondary processing feedstock has a polycyclic naphthene content of not greater than about 25 wt %, the process further comprises subjecting the secondary processing feedstock to aromatics extraction and/or said selective hydrotreatment and then using it as the catalytic cracking feedstock oil.

A5. The process of Item A1, wherein the first catalytic cracking reaction is carried out under the following conditions: a reaction temperature between about 520° C. and about 620° C., a reaction time between about 0.5 seconds and about 3.0 seconds, and a catalyst-to-oil ratio by weight between about 3:1 and about 15:1; and the second catalytic cracking reaction is carried out under the following conditions: a reaction temperature between about 420° C. and about 530° C., a reaction time between about 2 seconds and about 30 seconds, and a catalyst-to-oil ratio by weight between about 3:1 and about 18:1.

A6. The process of Item A1, wherein the first catalytic cracking reaction is carried out under the following conditions: a reaction temperature between about 530° C. and 600° C., a reaction time between about 0.8 seconds and about 2.0 seconds, and a catalyst-to-oil ratio by weight between about 4:1 and about 12:1;

the second catalytic cracking reaction is carried out under the following conditions: a reaction temperature between about 460° C. and about 510° C., a reaction time between about 3 seconds and about 15 seconds, and a catalyst-to-oil ratio by weight between about 4:1 and about 15:1.

A7. The process of Item A1, wherein the catalytic cracking reactor is a dual diameter riser, a fluidized bed, or a composite reactor composed of a conventional riser and a fluidized bed.

A8. The process of Item A7, wherein the dual diameter riser is sequentially provided with a pre-lifting section, a first reaction zone, a second reaction zone and an outlet zone from bottom to top in the vertical direction, which are coaxial and in fluid communication, a horizontal pipe connecting to a disengager is provided at the end of the outlet zone, the inner diameter of the first reaction zone is smaller than that of the second reaction zone, the inner diameter of the second reaction zone is larger than that of the outlet zone, the total height of the dual diameter riser is about 10-60 m, the catalytic cracking catalyst is fed into the pre-lifting section, the catalytic cracking feedstock oil is fed into the lower part of the first reaction zone, the first catalytic cracking reaction is carried out in the first reaction zone, and the second catalytic cracking reaction is carried out in the second reaction zone.

A9. The process of Item A8, wherein the joint region between the first and second reaction zones is provided with at least one quench medium inlet for injecting quench medium; and/or the second reaction zone is provided with a cooler, with the height of the cooler being about 50% to about 90% relative to the height of the second reaction zone.

A10. The process of Item A9, wherein the quench medium is selected from the group consisting of a chilling agent, a cooled regenerated catalyst, a cooled semi-regenerated catalyst, and a fresh catalyst, and combinations thereof, and wherein the chilling agent is selected from the group consisting of liquefied gases, crude gasolines, stabilized gasolines, light cycle oil fractions, heavy cycle oil fractions, water, and combinations thereof.

A11. The process of Item A1, wherein the catalytic cracking catalyst comprises a cracking active component and a support; the cracking active component comprises a FAU-type zeolite present in an amount of 0-100 wt %, preferably 10-90 wt %, and a pentasil zeolite present in an amount of 0-100 wt %, preferably 10-90 wt %, on a dry basis; the FAU-type zeolite is selected from the group consisting of Y-type zeolites, HY-type zeolites, ultrastable Y-type zeolites, and combinations thereof, the pentasil zeolite is selected from the group consisting of ZSM-5 zeolites, high-silica zeolites, ferrierites, and combinations thereof, and the pentasil zeolite may or may not comprise rare earth and/or phosphorus.

A12. The process of Item A1 or A4, wherein the selective hydrotreatment is carried out under the following conditions: a hydrogen partial pressure between 10.0 MPa and 30.0 MPa, a reaction temperature between 300° C. and 500° C., a liquid hourly space velocity between about 0.1 h⁻¹ and about 10.0 h⁻¹, and a hydrogen-to-oil ratio by volume between 100 Nm³/m³ and 1500 Nm³/m³.

A13. The process of Item A1 or A4, wherein the hydrotreating catalyst comprises a hydrotreating active component selected from the group consisting of Group VIB non-noble metals, Group VIII non-noble metals, and combinations thereof, and a support selected from the group consisting of alumina, silica, amorphous silica-alumina, and combinations thereof.

A14. The process of Item A1, wherein the extraction refining of step (4) is carried out under the following conditions: an extraction solvent selected from the group consisting of sulfolane, dimethyl sulfoxide, N-formylmorpholine, tetraethylene glycol, triethylene glycol, and N-methyl pyridine, and combinations thereof, a temperature of about 50-110° C., and a weight ratio of extraction solvent to gasoline of about 2-6.

A15. The process of Item A4, wherein the aromatics extraction is carried out under the following conditions: a temperature of about 50° C. to about 70° C., a solvent-to-feedstock ratio by weight of about 0.5 to about 2, a solvent selected from the group consisting of furfural, dimethyl sulfoxide, dimethylformamide, monoethanolamine, ethylene glycol, and 1,2-propanediol, and combinations thereof.

A16. The process of Item A1 or A4, wherein the selective hydrotreatment is carried out under the following conditions: a hydrogen partial pressure between about 6.0 MPa and about 30.0 MPa, a reaction temperature between about 300° C. and about 450° C., a liquid hourly space velocity between about 0.1 h⁻¹ and about 10.0 h⁻¹, and a hydrogen-to-oil ratio by volume between about 300 Nm³/m³ and about 3000 Nm³/m³; preferably, a hydrogen partial pressure between about 8 MPa and about 20 MPa, a reaction temperature between about 330° C. and about 430° C., a liquid hourly space velocity between about 0.2 h⁻¹ and about 5 h⁻¹, and a hydrogen-to-oil ratio by volume between about 500 Nm³/m³ and about 2500 Nm³/m³.

B1. A catalytic cracking process, comprising the following steps:
a) providing a catalytic cracking feedstock oil having a polycyclic naphthene content of greater than about 25 wt %, preferably greater than about 40 wt %, based on the weight of the catalytic cracking feedstock oil;
b) contacting the catalytic cracking feedstock oil with a catalytic cracking catalyst in a catalytic cracking reactor, and subjecting the mixture to a first catalytic cracking reaction and a second catalytic cracking reaction sequentially under different reaction conditions to obtain a catalytic cracking product;
c) separating the resulting catalytic cracking product to obtain a liquefied gas fraction comprising isobutane and a gasoline fraction comprising light aromatics; and
d) optionally, recovering isobutane from the liquefied gas fraction and/or recovering light aromatics from the gasoline fraction.

B2. The process of Item B1, wherein the separation in the step c) also produces a light cycle oil fraction, a heavy cycle oil fraction, and optionally a slurry oil, and the process further comprises the steps of:
e) subjecting at least a portion of the light cycle oil fraction, the heavy cycle oil fraction, and the optional slurry oil obtained in the step c) to a hydrotreatment to obtain a hydrogenated tail oil; and
f) recycling at least a portion of the resulting hydrogenated tail oil to the catalytic cracking reactor.

B3. The process of Item B1 or B2, wherein the step a) further comprises subjecting an initial feedstock oil having a polycyclic naphthene content of not greater than about 25 wt % to a pretreatment to obtain the catalytic cracking feedstock oil having a polycyclic naphthene content of greater than about 25 wt %, preferably greater than about 40 wt %.

B4. The process of Item B3, wherein the pretreatment includes aromatics extraction and/or hydrotreatment.

B5. The process of Item B2 or B4, wherein the hydrotreatment of step e) and/or the hydrotreatment performed as the pretreatment is carried out under the following conditions: a hydrogen partial pressure between about 6.0 and about 30.0 MPa; a reaction temperature between about 300° C. and about 450° C.; a liquid hourly space velocity between about 0.1 h⁻¹ and about 10.0 h⁻¹; a hydrogen-to-oil ratio by volume between about 300 Nm³/m³ and about 3000 Nm³/m³.

B6. The process of Item B2 or B4, wherein the hydrotreatment of step e) and/or the hydrotreatment performed as the pretreatment is carried out under the following conditions: a hydrogen partial pressure between about 8 MPa and about 20 MPa; a reaction temperature between about 330° C. and about 430° C.; a liquid hourly space velocity between about 0.2 h⁻¹ and about 5 h⁻¹; a hydrogen-to-oil ratio by volume between about 500 Nm³/m³ and about 2500 Nm³/m³.

B7. The process of any one of Items B4-B6, wherein the hydrotreatment of step e) and/or the hydrotreatment performed as the pretreatment is carried out in the presence of a hydrotreating catalyst comprising a hydrotreating active component preferably selected from the group consisting of Group VIB non-noble metals, Group VIII non-noble metals, and combinations thereof, and a support preferably selected from the group consisting of alumina, silica, amorphous silica-alumina, and combinations thereof.

B8. The process of any one of Items B4-B6, wherein the aromatics extraction is carried out under the following conditions: a temperature between about 50° C. and about 70° C., a solvent-to-feedstock ratio by weight of about 0.5-2, and a solvent selected from the group consisting of furfural, dimethyl sulfoxide, dimethylformamide, monoethanolamine, ethylene glycol, 1,2-propanediol, and combinations thereof.

B9. The process of any one of the preceding Items, wherein the catalytic cracking feedstock oil or the initial feedstock oil is selected from the group consisting of deep-hydrogenated light cycle oil, coker gas oil from delayed coker, catalytic cracking light cycle oil, catalytic cracking heavy cycle oil, FCC gas oil, slurry oil, hydrocracked diesel oil, residuum hydrocracked diesel oil, wax oil hydrocracked diesel oil, biodiesel, diesel fraction of shale oil, diesel fraction from coal liquefaction, atmospheric overhead oil, distillate oil extracted from atmospheric column, straight-run vacuum gas oil, hydrogenated wax oil, coker gas oil, deasphalted oil, extract oil, raffinate oil, atmospheric residuum, vacuum residuum, hydrogenated tail oils obtained from the above feedstock oils by hydrogenation, and combinations thereof.

B10. The process of any one of the preceding Items, wherein: the first catalytic cracking reaction is carried out under the following conditions: a reaction temperature between about 520° C. and about 620° C.; a reaction time between about 0.5 seconds and about 3.0 seconds; and a catalyst-to-oil ratio by weight between about 3:1 and about 15:1;
the second catalytic cracking reaction is carried out under the following conditions: a reaction temperature between about 480° C. and about 600° C.; a reaction time between about 2 seconds and about 30 seconds; a catalyst-to-oil ratio by weight between about 3:1 and about 18:1.

B11. The process of any one of the preceding Items, wherein: the first catalytic cracking reaction is carried out under the following conditions: a reaction temperature between about 530° C. and 600° C.; a reaction time between about 0.8 seconds and about 2.0 seconds; and a catalyst-to-oil ratio by weight between about 4:1 and about 12:1; and the second catalytic cracking reaction is carried out under the following conditions: a reaction temperature between about 500° C. and about 550° C.; a reaction time between about 3 seconds and about 15 seconds; and a catalyst-to-oil ratio by weight between about 4:1 and about 15:1.

B12. The process of any one of the preceding Items, wherein the catalytic cracking reactor is a conventional riser reactor, an equal-linear-velocity riser reactor, a dual diameter riser reactor, a fluidized bed reactor, or a composite reactor consisting of a conventional riser and a fluidized bed.

B13. The process of any one of the preceding Items, wherein the catalytic cracking reactor is a dual diameter riser reactor, the dual diameter riser reactor is sequentially provided with a pre-lifting section, a first reaction zone, a second reaction zone and an outlet zone from bottom to top in the vertical direction, which are coaxial and in fluid communication, the inner diameter of the first reaction zone is smaller than that of the second reaction zone, the inner diameter of the second reaction zone is larger than that of the outlet zone, the catalytic cracking catalyst is fed into the pre-lifting section, the catalytic cracking feedstock oil is fed into the lower part of the first reaction zone, the first catalytic cracking reaction is carried out in the first reaction zone, and the second catalytic cracking reaction is carried out in the second reaction zone.

B14. The process of Item B13, wherein the joint region between the first and second reaction zones is provided with at least one quench medium inlet for injecting quench medium; and/or the second reaction zone is provided with a cooler, with the height of the cooler being about 50% to about 90% relative to the height of the second reaction zone.

B15. The process of Item B14, wherein the quench medium is selected from the group consisting of a chilling agent, a cooled regenerated catalyst, a cooled semi-regenerated catalyst, a fresh catalyst, and combinations thereof; and wherein the chilling agent is selected from the group consisting of liquefied gases, crude gasolines, stabilized gasolines, light cycle oils, heavy cycle oils, water, and combinations thereof.

B16. The process of any one of the preceding Items, wherein the catalytic cracking catalyst comprises a cracking active component and a support; the cracking active component comprises about 0-100 wt % of FAU-type zeolite and about 0-100 wt % of pentasil zeolite, wherein the total amount of the FAU-type zeolite and the pentasil zeolite is 100 wt %, based on the weight of the cracking active component on a dry basis.

B17. The process of any one of the preceding Items, wherein the catalytic cracking catalyst comprises a cracking active component and a support; the cracking active component comprises about 10-90 wt % of FAU-type zeolite and about 10-90 wt % of pentasil zeolite, wherein the total amount of the FAU-type zeolite and the pentasil zeolite is 100 wt %, based on the weight of the cracking active component on a dry basis.

B18. The process of Item B16 or B17, wherein the FAU-type zeolite is selected from the group consisting of Y-type zeolites, HY-type zeolites, ultrastable Y-type zeolites, and combinations thereof; the pentasil zeolite is selected from the group consisting of ZSM-5 zeolites, high-silica zeolites, ferrierites, and combinations thereof, optionally containing rare earth and/or phosphorus.

B19. The process of any one of the preceding Items, wherein the step d) further comprises recovering light aromatics from the gasoline fraction by extraction refining.

B20. The process of Item B19, wherein the extraction refining is carried out under the following conditions: an extraction solvent selected from the group consisting of sulfolane, dimethyl sulfoxide, N-formylmorpholine, tetraethylene glycol, triethylene glycol, N-methylpyridinone, and combinations thereof, a temperature between about 50° C. and about 110° C., and a weight ratio of extraction solvent to gasoline fraction between about 2 and about 6.

EXAMPLES

The present application will be further illustrated by the following examples, but is not to be construed as being limited thereto.

Feedstocks and Reagents

The properties of the feedstock oils used in the following examples and comparative examples are shown in Tables 1 and 2.

TABLE 1

Properties of feedstock oils used in Examples 1-2 and Comparative Examples 1-2

| | Feedstock oil No. | | | | |
|---|---|---|---|---|---|
| | A | A' | B | C | D |
| | Type of feedstock oil | | | | |
| | Hydrogenated distillate oil | Hydrogenated tail oil | Light cycle oil | Hydrogenated light cycle oil | Vacuum resid |
| Density (20° C.), kg/m$^3$ | 895.3 | 930.9 | 943.2 | 854.6 | 890.5 |
| Element content, wt % | | | | | |
| Nitrogen | <0.1 | <0.01 | 0.64 | <0.01 | 0.29 |
| Sulfur | <0.1 | <0.01 | 1.11 | <0.01 | 0.13 |
| Carbon | 86.89 | 87.91 | 88.77 | 86.72 | 86.40 |
| Hydrogen | 13.01 | 12.08 | 9.48 | 13.27 | 13.18 |

TABLE 1-continued

Properties of feedstock oils used in Examples 1-2 and Comparative Examples 1-2

| | Feedstock oil No. | | | | |
|---|---|---|---|---|---|
| | A | A' | B | C | D |
| | Type of feedstock oil | | | | |
| | Hydrogenated distillate oil | Hydrogenated tail oil | Light cycle oil | Hydrogenated light cycle oil | Vacuum resid |
| Hydrocarbon group composition, wt % | | | | | |
| Paraffins | 20.32 | 9.4 | 10.60 | 18.60 | 39.46 |
| Naphthenes | 56.23 | 55.0 | 4.10 | 66.30 | 25.87 |
| Monocyclic | 8.00 | 1.8 | 2.21 | 9.31 | 12.51 |
| Bicyclic | 35.68 | 6.9 | 1.19 | 40.89 | 5.70 |
| Tricyclic | 13.65 | 24.2 | 0.70 | 16.10 | 3.73 |
| Tetracyclic and higher | 0.00 | 22.1 | 0.00 | 0.00 | 3.93 |
| Aromatics | 23.45 | 35.60 | 85.30 | 15.10 | 24.20 |
| Monocyclic | 11.95 | 19.6 | 2.50 | 14.10 | 12.85 |
| Bicyclic | 6.50 | 9.6 | 74.00 | 1.00 | 6.65 |
| Tricyclic and higher | 5.00 | 6.4 | 8.80 | 0.00 | 4.70 |
| Resins | 0.00 | 0 | 0.00 | 0.00 | 10.27 |
| Asphaltenes | 0.00 | 0 | 0.00 | 0.00 | 0.20 |

Note:
"—" means not measured.

TABLE 2

Properties of feedstock oils used in Examples 3-4 and Comparative Examples 3-4

| | Feedstock oil No. | | | |
|---|---|---|---|---|
| | E | F | G | G' |
| | Type of feedstock oil | | | |
| | Vacuum gas oil | Raffinate oil of vacuum gas oil | Extract oil of vacuum gas oil | Hydrogenated tail oil |
| Type of hydrocarbons/wt % | | | | |
| Paraffins | 18.4 | 29.6 | 4.5 | 6.0 |
| Naphthenes | 25.9 | 40.1 | 6.2 | 58.0 |
| Monocyclic | 8.5 | 13.2 | 2.1 | 29.0 |
| Bicyclic | 7.2 | 11.1 | 1.7 | 20.5 |
| Tricyclic and higher | 10.2 | 15.8 | 2.5 | 8.5 |
| Aromatics | 55.7 | 30.3 | 89.3 | 36.0 |
| Monocyclic | 27.0 | 17.3 | 44.1 | 19.3 |
| Bicyclic | 18.4 | 9.2 | 25.9 | 12.2 |
| Tricyclic and higher | 10.3 | 3.8 | 19.3 | 4.5 |
| Resins | 0.0 | 0.0 | 0.0 | 0.0 |
| Asphaltenes | 0.0 | 0.0 | 0.0 | 0.0 |
| Physical Properties | | | | |
| Density (20° C.), (g/cm$^3$) | 0.91 | — | — | — |
| Distillation range, ° C. | | | | |
| 10 wt % | 367 | — | — | — |
| 50 wt % | 462 | — | — | — |
| 90 wt % | 555 | — | — | — |
| S/wt % | 0.5 | — | — | <0.1 |
| N/wt % | 0.09 | — | — | <0.1 |

TABLE 2-continued

Properties of feedstock oils used in Examples 3-4 and Comparative Examples 3-4

| | Feedstock oil No. | | | |
|---|---|---|---|---|
| | H | I | J | J' |
| | Type of feedstock oil | | | |
| | Vacuum residue | Raffinate oil of vacuum residue | Extract oil of vacuum residue | Hydrogenated tail oil |
| Type of hydrocarbons/wt % | | | | |
| Paraffins | 5.9 | 10.5 | 1.9 | 10.0 |
| Naphthenes | 30.3 | 46.3 | 14.3 | 45.2 |
| Monocyclic | 9.5 | 13.51 | 4.49 | 15.2 |
| Bicyclic | 8.8 | 13.45 | 4.25 | 20.5 |
| Tricyclic and higher | 12.0 | 19.34 | 5.56 | 9.5 |
| Aromatics | 45.1 | 31.5 | 56.2 | 33.0 |
| Monocyclic | 12.3 | 7.89 | 16.33 | 20.1 |
| Bicyclic | 8.9 | 6.22 | 11.11 | 7.3 |
| Tricyclic and higher | 23.9 | 17.39 | 28.76 | 5.6 |
| Resins | 17.7 | 11.6 | 26.1 | 11.8 |
| Asphaltenes | 1.0 | 0.1 | 1.5 | 0.0 |
| Physical Properties | | | | |
| Density (20° C.), (g/cm$^3$) | 0.92 | — | — | — |
| Distillation range, ° C. | | | | |
| 10 wt % | >535 | — | — | — |
| 50 wt % | — | — | — | — |
| 90 wt % | — | — | — | — |
| S/wt % | 0.2 | — | — | 0.06 |
| N/wt % | 0.3 | — | — | 0.2 |

Note:
"—" means not measured.

The catalytic cracking catalyst IBA-1 used in the following examples and comparative examples comprises high-silica Y zeolite and ZRP zeolite as cracking active components in a weight ratio of 30 wt % of high-silica Y zeolite and 70 wt % of ZRP zeolite. The catalyst was prepared according to the following procedure:

969 g of halloysite (available from China Kaolin Clay Co., Ltd., with solid content of 73%) was slurried in 4300 g of deionized water, 781 g of pseudoboehmite (available from Shandong Zibo Aluminum Plant, with solid content of 64%) and 144 ml of hydrochloric acid (with concentration of 30% and specific gravity of 1.56) were added and stirred evenly, then the mixture was left to stand at 60° C. and aged for 1 hour, the pH value was kept in a range between 2 and 4; the mixture was cooled to normal temperature, then a pre-prepared slurry containing 800 g of high-silica Y zeolite (dry basis) (available from Qilu Catalyst Factory of Sinopec Catalyst Co., Ltd.) and 2000 g of ZRP zeolite (available from Qilu Catalyst Factory of Sinopec Catalyst Co., Ltd.) containing chemical water were added and stirred evenly, and the resultant was spray dried and washed off free Na$^+$ to obtain a catalyst. The catalyst thus obtained was aged at 800° C. in a 100% steam atmosphere for 12 hours to obtain the catalyst IBA-1, of which the physicochemical properties are shown in Table 3.

The catalytic cracking catalysts, commercially available under the names CGP-1, MLC-500 and DMMC-1, used in the following examples and comparative examples were all obtained from the Qilu Catalyst Factory of Sinopec Catalyst Co., Ltd., of which the physicochemical properties are shown in Table 3.

TABLE 3

Physicochemical properties of the catalytic cracking catalysts used in the examples and comparative examples

| Name (R) | IBA-1 | CGP-1 | MLC-500 | DMMC-1 |
|---|---|---|---|---|
| Micro-activity | 65 | 65 | 65 | 65 |
| Total specific surface area/(m$^2$ · g$^{-1}$) | 132 | 88 | 98 | 126 |
| Total pore volume/(cm$^3$ · g$^{-1}$) | 0.24 | 0.147 | 0.148 | 0.26 |

The hydrotreating catalyst commercially available under the name RN-32V and the protective agent commercially available under the names RG-30A, RG-30B, RG-1, used in the following examples and comparative examples, were all obtained from the Sinopec Catalyst Co., Ltd., and the loading ratio of the hydrotreating catalyst and the protective agent in the hydrogenation unit was 95:5 by volume.

Measurement Method

The micro-activity (MAT) of the catalytic cracking catalyst was measured in accordance with the standard method of RIPP 92-90 (see "Petrochemical Analysis Methods (RIPP Test Methods)", edited by Cuiding YANG et al., Science Press, September 1990, First Edition, pages 263-268) under the following conditions: 5.0 g of catalyst; 1.56 g of inputted oil; a reaction time of 70 seconds; a reaction temperature of 460° C.; a catalyst-to-oil ratio of 3.2; and a space velocity of 16h$^{-1}$.

The specific surface area and the total pore volume of the catalytic cracking catalyst were measured using AS-3, AS-6 Static Nitrogen Adsorption Instrument manufactured by Quantachrome Instruments according to the following procedure: the sample was placed in a sample processing system, evacuated at 300° C. to a pressure of $1.33 \times 10^{-2}$ Pa, kept at the temperature and the pressure for 4 h, to obtain a purified sample; the adsorption quantity and desorption quantity of nitrogen on the purified sample were measured at a liquid nitrogen temperature of −196° C. under the conditions of different specific pressures $P/P_0$ to obtain an $N_2$ adsorption-desorption isothermal curve; and then the total specific surface area, the micropore specific area and the mesopore specific area were calculated using a two-parameter BET equation, taking the adsorption quantity at the specific pressure $P/P_0$=0.98 or less as the total pore volume of the sample.

Example 1-A

Following the process flow shown in FIG. 1, a preheated catalytic cracking feedstock oil A was contacted with a catalyst IBA-1 in a medium-sized dual diameter riser used as the catalytic cracking device to carry out a catalytic cracking reaction. The preheated feedstock oil A was fed into a dual diameter riser reactor shown in FIG. 1, contacted with a hot catalytic cracking catalyst IBA-1 in a first reaction zone and a second reaction zone to carry out a first catalytic cracking reaction and a second catalytic cracking reaction in the presence of steam, and the resulting catalytic cracking product was separated to obtain a dry gas, a liquefied gas rich in isobutane, a gasoline rich in aromatics, a light cycle oil and a heavy cycle oil (with no slurry oil); the light cycle oil was discharged from the device, the heavy cycle oil was recycled to a hydrogenation unit for hydrotreatment, and the resulting hydrogenated tail oil A' was recycled to the riser reactor for catalytic cracking reaction; the spent catalyst was sent to a regenerator after being stripped, and then recycled after being regenerated via coke burning. The properties of the feedstock oil are shown in Table 1, the operating conditions are shown in Table 4, the product distribution is shown in Table 5, and the properties of the product obtained from gasoline by extraction refining are shown in Table 5.

Example 1-B

The present example was carried out in a similar manner as described in Example 1, using the conventional catalytic cracking catalyst CGP-1. Preheated catalytic cracking feedstock oil A was fed into a dual diameter riser reactor shown in FIG. 1, contacted with a hot catalytic cracking catalyst CGP-1 in a first reaction zone and a second reaction zone to carry out a first catalytic cracking reaction and a second catalytic cracking reaction in the presence of steam, and the resulting catalytic cracking product was separated to obtain a dry gas, a liquefied gas rich in isobutane, a gasoline rich in aromatics, a light cycle oil and a heavy cycle oil (with no slurry oil); the light cycle oil was discharged from the device, the heavy cycle oil was recycled to a hydrogenation unit for hydrotreatment, and the resulting hydrogenated tail oil was recycled to the riser reactor for catalytic cracking reaction; the spent catalyst was sent to a regenerator after being stripped, and then recycled after being regenerated via coke burning. The properties of the feedstock oil are shown in Table 1, the operating conditions are shown in Table 4, the product distribution is shown in Table 5, and the properties of the product obtained from gasoline by extraction refining are shown in Table 5.

Example 1-C

The present example was carried out in a similar manner as described in Example 1, using the conventional catalytic cracking catalyst MLC-500. Preheated catalytic cracking feedstock oil A was fed into a conventional riser reactor, and a quench medium was injected into the middle part of the conventional riser reactor to form a first reaction zone at the lower part and a second reaction zone at the upper part. The feedstock oil A was contacted with a hot catalytic cracking catalyst MLC-500 in the first reaction zone and the second reaction zone to carry out a first catalytic cracking reaction and a second catalytic cracking reaction in the presence of steam, and the resulting catalytic cracking product was separated to obtain a dry gas, a liquefied gas rich in isobutane, a gasoline rich in aromatics, a light cycle oil and a heavy cycle oil (with no slurry oil); the light cycle oil was discharged from the device, the heavy cycle oil was recycled to a hydrogenation unit for hydrotreatment, and the resulting hydrogenated tail oil was recycled to the riser reactor for catalytic cracking reaction; the spent catalyst was sent to a regenerator after being stripped, and then recycled after being regenerated via coke burning. The properties of the feedstock oil are shown in Table 1, the operating conditions are shown in Table 4, the product distribution is shown in Table 5, and the properties of the product obtained from gasoline by extraction refining are shown in Table 5.

Example 1-D

The present example was carried out in a similar manner as described in Example 1, using the conventional catalytic cracking catalyst DMMC-1. Preheated catalytic cracking feedstock oil A was fed into a composite reactor composed of a riser reactor and a fluidized bed, in which the riser reactor served as a first reaction zone, and the fluidized bed served as a second reaction zone. The feedstock oil A was contacted with a hot catalytic cracking catalyst DMMC-1 in the first reaction zone and the second reaction zone to carry out a first catalytic cracking reaction and a second catalytic cracking reaction in the presence of steam, and the catalytic cracking product was separated to obtain a dry gas, a liquefied gas containing isobutane, a gasoline rich in aromatics, a light cycle oil and a heavy cycle oil (with no slurry oil); the light cycle oil was discharged from the device, the heavy cycle oil was recycled to a hydrogenation unit for hydrotreatment, and the resulting hydrogenated tail oil was recycled to the riser reactor for catalytic cracking reaction; the spent catalyst was sent to a regenerator after being stripped, and then recycled after being regenerated via coke burning. The properties of the feedstock oil are shown in Table 1, the operating conditions are shown in Table 4, the product distribution is shown in Table 5, and the properties of the product obtained from gasoline by extraction refining are shown in Table 5.

Comparative Example 1-A

The present comparative example was carried out in a similar manner as described in Example 1, using a feedstock oil D having a low polycyclic naphthene content. Preheated feedstock oil D was fed into a dual diameter riser reactor shown in FIG. 1, contacted and reacted with a hot catalytic cracking catalyst CGP-1 in the presence of steam, and the catalytic cracking product was separated to obtain a dry gas, a liquefied gas, a gasoline, a light cycle oil, a heavy cycle oil and a slurry oil; and the light cycle oil and the slurry oil were discharged from the device, the heavy cycle oil was recycled to a hydrogenation unit for hydrotreatment, and then returned to the riser reactor, and the spent catalyst was sent to a regenerator after being stripped, and then recycled after being regenerated via coke burning. The properties of the feedstock oil are shown in Table 1, the operating conditions are shown in Table 4, the product distribution is shown in Table 5, and the properties of the product obtained from gasoline by extraction refining are shown in Table 5.

Comparative Example 1-B

The present comparative example was carried out in a similar manner as described in Example 1, using the conventional catalytic cracking catalyst MLC-500. Preheated feedstock oil A was fed into a conventional riser reactor, contacted and reacted with a hot catalytic cracking catalyst in the presence of steam, and the catalytic cracking product was separated to obtain a dry gas, a liquefied gas, a gasoline, a light cycle oil, a heavy cycle oil and a slurry oil; and the light cycle oil and the slurry oil were discharged from the device, the heavy cycle oil was recycled to a hydrogenation unit for hydrotreatment, and then returned to the riser reactor, and the spent catalyst was sent to a regenerator after being stripped, and then recycled after being regenerated via coke burning. The properties of the feedstock oil are shown in Table 1, the operating conditions are shown in Table 4, the product distribution is shown in Table 5, and the properties of the product obtained from gasoline by extraction refining are shown in Table 5.

Comparative Example 1-C

The present comparative example was carried out in a similar manner as described in Example 1, using the catalytic cracking catalyst IBA-1. Preheated feedstock oil A was fed into a conventional riser reactor, contacted and reacted with a hot catalytic cracking catalyst in the presence of steam, and the catalytic cracking product was separated to obtain a dry gas, a liquefied gas, a gasoline, a light cycle oil, a heavy cycle oil and a slurry oil; and the light cycle oil and the slurry oil were discharged from the device, the heavy cycle oil was recycled to a hydrogenation unit for hydrotreatment, and then returned to the riser reactor, and the spent catalyst was sent to a regenerator after being stripped, and then recycled after being regenerated via coke burning. The properties of the feedstock oil are shown in Table 1, the operating conditions are shown in Table 4, the product distribution is shown in Table 5, and the properties of the product obtained from gasoline by extraction refining are shown in Table 5.

TABLE 4

Operating conditions employed in Examples 1-A to 1-D and Comparative Examples 1-A to 1-C

| Item | Ex. 1-A | Ex. 1-B | Ex. 1-C | Ex. 1-D |
|---|---|---|---|---|
| Feedstock oil No. | A | A | A | A |
| Catalyst type | IBA-1 | CGP-1 | MLC-500 | DMMC-1 |
| Reactor type | Dual diameter riser reactor | Dual diameter riser reactor | Conventional riser reactor | Riser + fluidized bed |
| Reaction temperature, °C. | | | | |
| First reaction zone | 550 | 550 | 550 | 570 |
| Second reaction zone | 530 | 530 | 530 | 550 |
| Reaction time, seconds | | | | |
| First reaction zone | 1.3 | 1.3 | 1.1 | 3.1 |
| Second reaction zone | 4.4 | 4.4 | 2.0 | 12.0 |
| Catalyst-to-oil ratio | 5.0 | 5.0 | 5.0 | 6.0 |
| Water-to-oil ratio | 0.1 | 0.1 | 0.1 | 0.25 |
| Bed temperature, °C. | — | — | — | 550 |
| Space velocity of the bed, $h^{-1}$ | — | — | — | 4 |
| Hydrogenation unit | | | | |
| Reaction temperature, °C. | 370 | 370 | 370 | 370 |
| Reaction pressure, MPa | 17.0 | 17.0 | 17.0 | 17.0 |
| LHSV, $h^{-1}$ | 0.5 | 0.5 | 0.5 | 0.5 |
| Hydrogen-to-oil ratio by volume, $Nm^3/m^3$ | 1000 | 1000 | 1000 | 1000 |
| Extraction refining unit | | | | |
| Extraction solvent | Sulfolane | Sulfolane | Sulfolane | Sulfolane |
| Extraction temperature, °C. | 65 | 65 | 65 | 65 |
| Solvent-to-oil ratio by weight | 4 | 4 | 4 | 4 |

TABLE 4-continued

Operating conditions employed in Examples 1-A to 1-D and Comparative Examples 1-A to 1-C

| Item | Comp. Ex. 1-A | Comp. Ex. 1-B | Comp. Ex. 1-C |
|---|---|---|---|
| Feedstock oil No. | D | A | A |
| Catalyst type | CGP-1 | MLC-500 | IBA-1 |
| Reactor type | Dual diameter riser reactor | Conventional riser reactor | Conventional riser reactor |
| Reaction temperature, °C | | 530 | 530 |
| First reaction zone | 550 | — | — |
| Second reaction zone | 530 | — | — |
| Reaction time, seconds | 5.2 | 3.1 | 3.1 |
| First reaction zone | 1.2 | — | — |
| Second reaction zone | 4.0 | — | — |
| Catalyst-to-oil ratio | 5.0 | 5.0 | 5.0 |
| Water-to-oil ratio | 0.1 | 0.1 | 0.1 |
| Bed temperature, °C | — | — | — |
| Space velocity of the bed, $h^{-1}$ | — | — | — |
| Hydrogenation unit | | | |
| Reaction temperature, °C | 370 | 370 | 370 |
| Reaction pressure, MPa | 17.0 | 17.0 | 17.0 |
| Volumetric space velocity, $h^{-1}$ | 0.5 | 0.5 | 0.5 |
| Hydrogen-to-oil ratio by volume, $Nm^3/m^3$ | 1000 | 1000 | 1000 |
| Extraction refining unit | | | |
| Extraction solvent | Sulfolane | Sulfolane | Sulfolane |
| Extraction temperature, °C | 65 | 65 | 65 |
| Solvent-to-oil ratio by weight | 4 | 4 | 4 |

Note:
"—" means not measured.

TABLE 5

Results of Examples 1-A to 1-D and Comparative Examples 1-A to 1-C

| Item | Ex. 1-A | Ex. 1-B | Ex. 1-C | Ex. 1-D |
|---|---|---|---|---|
| Feedstock oil No. | A | A | A | A |
| Catalyst type | IBA-1 | CGP-1 | MLC-500 | DMMC-1 |
| Reactor type | Dual diameter riser reactor | Dual diameter riser reactor | Conventional riser reactor | Riser + fluidized bed |
| Product distribution, wt % | | | | |
| Dry gas | 2.30 | 2.81 | 2.91 | 7.79 |
| Liquefied gas | 37.71 | 28.52 | 16.31 | 42.71 |
| Propylene | 13.20 | 7.17 | 3.60 | 19.27 |
| Isobutene | 2.49 | 2.71 | 2.03 | 5.35 |
| Isobutane | 14.32 | 13.21 | 8.37 | 2.46 |
| Gasoline | 49.47 | 51.62 | 62.16 | 35.30 |
| Benzene | 2.06 | 1.02 | 0.59 | 2.71 |
| Toluene | 9.97 | 4.59 | 3.92 | 9.31 |
| Xylene | 13.14 | 6.58 | 6.97 | 12.26 |
| BTX | 25.17 | 12.19 | 11.48 | 24.28 |
| Light cycle oil | 5.85 | 12.41 | 13.80 | 7.01 |
| Slurry oil | 0.0 | 0.0 | 0 | 0.0 |
| Coke | 4.67 | 4.64 | 4.82 | 7.19 |
| Total | 100.00 | 100.00 | 100.00 | 100.00 |

TABLE 5-continued

Results of Examples 1-A to 1-D and Comparative Examples 1-A to 1-C

| | Comp. Ex. 1-A | Comp. Ex. 1-B | Comp. Ex. 1-C |
|---|---|---|---|
| | | Feedstock oil No. | |
| | D | A | A |
| | | Catalyst type | |
| | CGP-1 | MLC-500 | IBA-1 |
| | | Reactor type | |
| Item | Dual diameter riser reactor | Conventional riser reactor | Conventional riser reactor |
| Product distribution, wt % | | | |
| Dry gas | 1.72 | 1.01 | 1.81 |
| Liquefied gas | 25.85 | 17.15 | 22.03 |
| Propylene | 9.2 | 5.82 | 7.18 |
| Isobutene | 2.71 | 2.63 | 3.13 |
| Isobutane | 5.88 | 2.98 | 7.94 |
| Gasoline | 51.06 | 55.61 | 46.25 |
| Benzene | 0.83 | 0.51 | 0.89 |
| Toluene | 5.77 | 3.41 | 4.89 |
| Xylene | 7.95 | 5.24 | 6.94 |
| BTX | 14.55 | 9.16 | 12.72 |
| Light cycle oil | 10.02 | 14.15 | 17.91 |
| Slurry oil | 5.07 | 6.19 | 6.87 |
| Coke | 6.28 | 5.89 | 5.13 |
| Total | 100.00 | 100.00 | 100.00 |

Example 2

Following the process flow shown in FIG. 2, an initial feedstock oil B was first subjected to hydrogenation saturation to obtain a catalytic cracking feedstock oil C. Preheated catalytic cracking feedstock oil C was fed into a dual diameter riser reactor shown in FIG. 2, contacted and reacted with a hot catalyst IBA-1 in the presence of steam, and the resulting catalytic cracking product was separated to obtain a dry gas, a liquefied gas rich in isobutane, a gasoline rich in aromatics, a light cycle oil and a heavy cycle oil (with no slurry oil); and the light cycle oil was discharged from the device, the heavy cycle oil was recycled to a hydrogenation unit for hydrotreatment, the resulting hydrogenated tail oil was recycled to the riser reactor for catalytic cracking reaction, the spent catalyst was sent to a regenerator after being stripped, and then recycled after being regenerated via coke burning. The properties of the feedstock oil are shown in Table 1, the operating conditions are shown in Table 6, the product distribution is shown in Table 7, and the properties of the product obtained from gasoline by extraction refining are shown in Table 7.

Comparative Example 2

Following the process flow shown in FIG. 1, the feedstock oil B was not subjected to hydrogenation, preheated feedstock oil B was directly fed into a dual diameter riser reactor shown in FIG. 1, contacted and reacted with a hot catalyst IBA-1 in the presence of steam, and the catalytic cracking product was separated to obtain a dry gas, a liquefied gas, a gasoline, a light cycle oil, a heavy cycle oil and a slurry oil; the light cycle oil and the slurry oil are discharged from the device, and the heavy cycle oil was recycled to the hydrogenation unit for hydrotreatment and then returned to the riser reactor; the spent catalyst was sent to a regenerator after being stripped, and then recycled after being regenerated via coke burning. The properties of the feedstock oil are shown in Table 1, the operating conditions are shown in Table 6, the product distribution is shown in Table 7, and the properties of the product obtained from gasoline by extraction refining are shown in Table 7.

TABLE 6

Operating conditions employed in Example 2 and Comparative Example 2

| | Ex. 2 | Comp. Ex. 2 |
|---|---|---|
| | Feedstock oil No. | |
| | B is | B is |
| | Catalyst type | |
| | IBA-1 | IBA-1 |
| | Reactor type | |
| Item | Dual diameter riser reactor | Dual diameter riser reactor |
| Reaction temperature, °C. | | |
| First reaction zone | 550 | 550 |
| Second reaction zone | 530 | 530 |
| Reaction time, seconds | | |
| First reaction zone | 1.3 | 1.3 |
| Second reaction zone | 4.4 | 4.4 |
| Catalyst-to-oil ratio | 5.0 | 5.0 |
| Water-to-oil ratio | 0.1 | 0.1 |
| Hydrogenation unit | | |
| Reaction temperature, °C. | 370 | |
| Reaction pressure, MPa | 12.0 | |
| LHSV, h$^{-1}$ | 0.6 | |
| Hydrogen-to-oil ratio by volume, Nm$^3$/m$^3$ | 900 | |
| Extraction refining unit | | |
| Extraction solvent | Sulfolane | Sulfolane |
| Extraction temperature, °C. | 65 | 65 |
| Solvent-to-oil ratio, w/w | 4 | 4 |

TABLE 7

Results of Example 2 and Comparative Example 2

| Item | Ex. 2 | Comp. Ex. 2 |
|---|---|---|
| Feedstock oil No. | B | B |
| Catalyst type | IBA-1 | IBA-1 |
| Reactor type | Dual diameter riser reactor | Dual diameter riser reactor |
| Product distribution, wt % | | |
| Dry gas | 2.21 | 3.55 |
| Liquefied gas | 25.41 | 10.77 |
| Propylene | 4.96 | 3.98 |
| Isobutene | 0.67 | 0.31 |
| Isobutane | 11.19 | 3.95 |
| Gasoline | 58.88 | 30.91 |
| Benzene | 2.05 | 1.72 |
| Toluene | 13.52 | 8.61 |
| Xylene | 20.17 | 10.50 |
| BTX | 35.74 | 20.83 |
| Light cycle oil | 11.51 | 47.52 |
| Slurry oil | 0.00 | 2.00 |
| Coke | 1.99 | 5.25 |
| Total | 100.00 | 100.00 |

Example 3

Following the process flow shown in FIG. 3, the vacuum distillate oil E used as a feedstock oil was processed through an aromatics extraction unit to obtain an extract oil G of the vacuum distillate oil and a raffinate oil F of the vacuum distillate oil, under the following conditions: a temperature of 60° C., a solvent-to-feedstock ratio by weight of 1.5, and a solvent of furfural. The extract oil G of the vacuum distillate oil was mixed with hydrogen, and then passed into a hydrogenation unit for hydrotreatment, obtaining a hydrogenated tail oil G' from the hydrogenation unit, preheated hydrogenated tail oil was mixed with the raffinate oil F of the vacuum distillate oil, and then fed into a dual diameter riser reactor shown in FIG. 3 as the catalytic cracking feedstock oil, contacted and reacted with a hot catalyst IBA-1 in the presence of steam, and the catalytic cracking product was separated to obtain a dry gas, a liquefied gas rich in isobutane, a gasoline rich in aromatics, a light cycle oil and a heavy cycle oil (with no slurry oil); the light cycle oil was discharged from the device, the heavy cycle oil was mixed with the extract oil G of the vacuum distillate oil, and then sent to the hydrogenation unit for hydrotreatment, and the resulting hydrogenated tail oil was recycled to the riser reactor for catalytic cracking reaction; the spent catalyst was sent to a regenerator after being stripped, and then recycled after being regenerated via coke burning. The properties of the feedstock oil are shown in Table 2, the operating parameters are shown in Table 8, the product distribution is shown in Table 9, and the properties of the product obtained from gasoline by extraction refining are shown in Table 9.

Comparative Example 3

Following the process flow shown in FIG. 1, the feedstock oil E was not subjected to extraction and hydrotreatment, preheated feedstock oil E was directly fed into a dual diameter riser reactor shown in FIG. 1, contacted and reacted with a hot catalyst IBA-1 in the presence of steam, and the catalytic cracking product was separated to obtain a dry gas, a liquefied gas, a gasoline, a light cycle oil, a heavy cycle oil and a slurry oil; wherein the light cycle oil and the slurry oil were discharged from the device, and the heavy cycle oil was recycled to the hydrogenation unit for hydrotreatment and then returned to the riser reactor; the spent catalyst was sent to a regenerator after being stripped, and then recycled after being regenerated via coke burning. The properties of the feedstock oil are shown in Table 2, the operating parameters are shown in Table 8, the product distribution is shown in Table 9, and the properties of the product obtained from gasoline by extraction refining are shown in Table 9.

Example 4

Following the process flow shown in FIG. 3, the vacuum residuum H used as a feedstock oil was processed through an aromatics extraction unit to obtain an extract oil J of the vacuum residuum and a raffinate oil I of the vacuum residuum, under the following conditions: a temperature of 60° C., a solvent-to-feedstock ratio by weight of 1.5, and a solvent of furfural. The extract oil J of the vacuum residuum was mixed with hydrogen, and then passed into a hydrogenation unit for hydrotreatment, obtaining a hydrogenated tail oil J' from the hydrogenation unit, preheated hydrogenated tail oil was mixed with the raffinate oil I of the vacuum residuum, and then fed into a dual diameter riser reactor shown in FIG. 3 as the catalytic cracking feedstock oil, contacted and reacted with a hot catalyst IBA-1 in the presence of steam, the catalytic cracking product was separated to obtain a dry gas, a liquefied gas rich in isobutane, a gasoline rich in aromatics, a light cycle oil and a heavy cycle oil (with no slurry oil), the light cycle oil was discharged from the device, the heavy cycle oil was mixed with the extract oil J of the vacuum residuum, then passed into the hydrogenation unit for hydrotreatment, and the resulting hydrogenated tail oil was recycled to the riser reactor for catalytic cracking reaction; the spent catalyst was sent to a regenerator after being stripped, and then recycled after being regenerated via coke burning. The properties of the feedstock oil are shown in Table 2, the operating parameters are shown in Table 8, the product distribution is shown in Table 9, and the properties of the product obtained from gasoline by extraction refining are shown in Table 9.

Comparative Example 4

Following the process flow shown in FIG. 1, the vacuum residuum H used as a feedstock oil was not subjected to extraction and hydrotreatment, preheated feedstock oil H was directly fed into a dual diameter riser reactor shown in FIG. 1, contacted and reacted with a hot catalyst IBA-1 in the presence of steam, and the catalytic cracking product was separated to obtain a dry gas, a liquefied gas, a gasoline, a light cycle oil, a heavy cycle oil and a slurry oil; in which the light cycle oil and the slurry oil were discharged from the device, and the heavy cycle oil was recycled to a hydrogenation unit for hydrotreatment and then returned to the riser reactor; the spent catalyst was passed into a regenerator after being stripped, and then recycled after being regenerated via coke burning. The properties of the feedstock oil are shown in Table 2, the operating parameters are shown in Table 8, the product distribution is shown in Table 9, and the properties of the product obtained from gasoline by extraction refining are shown in Table 9.

TABLE 8

Operating conditions employed in Examples 3-4 and Comparative Examples 3-4

| Item | Ex. 3 | Comp. Ex. 3 | Ex. 4 | Comp. Ex. 4 |
|---|---|---|---|---|
| Feedstock oil No. | E | E | H | H |
| Catalyst type | IBA-1 | IBA-1 | IBA-1 | IBA-1 |
| Reactor type | Dual diameter riser reactor | Dual diameter riser reactor | Dual diameter riser reactor | Dual diameter riser reactor |
| Reaction temperature, °C. | | | | |
| First reaction zone | 550 | 550 | 550 | 550 |
| Second reaction zone | 530 | 530 | 530 | 530 |
| Reaction time, seconds | | | | |
| First reaction zone | 1.3 | 1.3 | 1.3 | 1.3 |
| Second reaction zone | 4.4 | 4.4 | 4.4 | 4.4 |
| Catalyst-to-oil ratio | 5.0 | 5.0 | 5.0 | 5.0 |
| Water-to-oil ratio | 0.1 | 0.1 | 0.1 | 0.1 |
| Hydrogenation unit | | | | |
| Reaction temperature, °C. | 375 | | 385 | |
| Reaction pressure, MPa | 14.0 | | 16.0 | |
| LHSV, $h^{-1}$ | 0.7 | | 0.3 | |
| Hydrogen-to-oil ratio by volume, $Nm^3/m^3$ | 1200 | | 900 | |
| Extraction refining unit | | | | |
| Extraction solvent | Sulfolane | Sulfolane | Sulfolane | Sulfolane |
| Extraction temperature, °C. | 65 | 65 | 65 | 65 |
| Solvent-to-oil ratio by weight | 4 | 4 | 4 | 4 |

TABLE 9

Results of Examples 3-4 and Comparative Examples 3-4

| Item | Ex. 3 | Comp. Ex. 3 | Ex. 4 | Comp. Ex. 4 |
|---|---|---|---|---|
| Feedstock oil No. | E | E | H | H |
| Catalyst type | IBA-1 | IBA-1 | IBA-1 | IBA-1 |
| Reactor type | Dual diameter riser reactor | Dual diameter riser reactor | Dual diameter riser reactor | Dual diameter riser reactor |
| Product distribution, wt % | | | | |
| Dry gas | 2.49 | 1.52 | 2.79 | 3.14 |
| Liquefied gas | 36.81 | 20.71 | 33.83 | 16.51 |
| Propylene | 12.52 | 7.10 | 11.31 | 5.82 |
| Isobutene | 1.31 | 3.19 | 1.12 | 2.52 |
| Isobutane | 13.75 | 4.15 | 12.44 | 2.44 |
| Gasoline | 49.04 | 42.77 | 45.70 | 36.16 |
| Benzene | 1.91 | 0.87 | 1.86 | 0.81 |
| Toluene | 8.87 | 5.31 | 8.56 | 5.83 |
| Xylene | 12.84 | 7.35 | 12.77 | 7.95 |
| BTX | 23.62 | 13.53 | 23.19 | 14.59 |
| Light cycle oil | 6.70 | 24.87 | 8.18 | 23.86 |
| Slurry oil | 0.00 | 6.33 | 0.00 | 7.90 |
| Coke | 4.96 | 3.80 | 9.50 | 12.43 |
| Total | 100.00 | 100.00 | 100.00 | 100.00 |

As can be seen from the comparison of the results of the above examples and comparative examples, the process according to the present application enables the production of isobutane and/or light aromatics at a higher yield, particularly when a dual diameter riser reactor is used.

In the context hereinabove, the inventive concept of the present application has been described with reference to specific embodiments. However, it will be understood by those skilled in the art that various modifications and changes may be made without departing from the scope of the invention as defined in the appended claims. Accordingly, the specification and drawings should be interpreted in an illustrative rather than a restrictive manner, and all such modifications and changes are intended to be included within the scope of present application.

It is to be understood that certain features which are, for clarity, described herein in separate embodiments, may also be provided in combination in a single embodiment. Conversely, various features which are, for brevity, described in a single embodiment, may also be provided separately or in any subcombination.

The invention claimed is:

1. A catalytic cracking process, comprising:
   a) measuring a content of polycyclic naphthene in an initial feedstock oil;
   when the content of polycyclic naphthene is not greater than 25 wt % based on a total weight of the initial feedstock oil, pretreating the initial feedstock oil to obtain a catalytic cracking feedstock oil having a polycyclic naphthene content of greater than 25 wt %, based on a weight of the catalytic cracking feedstock oil,
   wherein the pretreating comprises subjecting the initial feedstock oil to aromatic extraction to produce an extract oil rich in polycyclic aromatics and a raffinate oil rich in polycyclic naphthenes, subjecting the extract oil to hydrotreatment to produce a hydrogenated oil, and
   combining the hydrogenated oil and the raffinate oil to obtain the catalytic cracking feedstock oil; or
   when the content of polycyclic naphthene is greater than 25 wt % based on the total weight of the initial feedstock oil, using the initial feedstock oil as the catalytic cracking feedstock oil,
   b) contacting the catalytic cracking feedstock oil obtained from step a) with a catalytic cracking catalyst in a catalytic cracking reactor, and subjecting a reaction mixture to a first catalytic cracking reaction and a second catalytic cracking reaction sequentially to obtain a catalytic cracking product;
   c) separating the catalytic cracking product to obtain a liquefied gas fraction comprising isobutane and a gasoline fraction comprising light aromatics; and
   d) optionally, recovering isobutane from the liquefied gas fraction and/or recovering light aromatics from the gasoline fraction,
   wherein the first catalytic cracking reaction is carried out at a reaction temperature between 520° C. and 620° C. for a reaction time between 0.5 seconds and 3.0 seconds at a catalyst-to-oil ratio by weight between 3:1 and 15:1, and
   the second catalytic cracking reaction is carried out at a reaction temperature between 480° C. and 600° C. for a reaction time between 2 seconds and 30 seconds at a catalyst-to-oil ratio by weight between 3:1 and 18:1,
   and wherein the catalytic cracking catalyst comprises a cracking active component and a support, and the cracking active component comprises 0 wt % to 100 wt % of FAU-type zeolite and 0 wt % to 100 wt % of pentasil zeolite, wherein a total amount of the FAU-type zeolite and the pentasil zeolite is 100 wt %, based on the weight of the cracking active component on a dry basis; the FAU-type zeolite is selected from the group consisting of Y-type zeolites, HY-type zeolites, ultrastable Y-type zeolites, and combinations thereof, and the pentasil zeolite is selected from the group consisting of ZSM-5 zeolites, high-silica zeolites, ferrierites, and combinations thereof.

2. The process according to claim 1, wherein the separation in the step c) produces the liquefied gas fraction, the gasoline fraction, a light cycle oil fraction, a heavy cycle oil fraction, and optionally a slurry oil, and the process further comprises the steps of:
   e) subjecting at least a portion of the light cycle oil fraction, the heavy cycle oil fraction, and the optional slurry oil obtained in the step c) to hydrotreatment to obtain a hydrogenated tail oil; and
   f) recycling at least a portion of the hydrogenated tail oil to the catalytic cracking reactor.

3. The process according to claim 2, wherein the hydrotreatment of step e) is carried out under a hydrogen partial pressure between 6.0 MPa and 30.0 MPa at a reaction temperature between 300° C. and 450° C., a liquid hourly space velocity between $0.1h^{-1}$ and $10.0 h^{-1}$, and a hydrogen-to-oil ratio by volume between 300 $Nm^3/m^3$ and 3000 $Nm^3/m^3$.

4. The process according to claim 2, wherein the hydrotreatment of step e) is carried out in the presence of a hydrotreating catalyst comprising a hydrotreating active component and a support, the hydrotreating active component is selected from the group consisting of Group VIB non-noble metals, Group VIII non-noble metals, and combinations thereof, and the support is selected from the group consisting of alumina, silica, amorphous silica-alumina, and combinations thereof.

5. The process according to claim 1, wherein the aromatic extraction is carried out at a temperature between 50° C. and 70° C., and a solvent-to-feedstock ratio by weight between 0.5 and 2 using a solvent selected from the group consisting of furfural, dimethyl sulfoxide, dimethylformamide, monoethanolamine, ethylene glycol, 1,2-propanediol, and combinations thereof.

6. The process according to claim 1, wherein:
   the first catalytic cracking reaction is carried out at 530° C. to 600° C. for 0.8 seconds to 2.0 seconds at the catalyst-to-oil ratio by weight between 4:1 and 12:1, and
   the second catalytic cracking reaction is carried out at 500° C. to 550° C. for 3 seconds to 15 seconds at the catalyst-to-oil ratio by weight between 4:1 and 15:1.

7. The process according to claim 1, wherein the catalytic cracking reactor is a conventional riser reactor, an equal-linear-velocity riser reactor, a dual diameter riser reactor, a fluidized bed reactor, or a composite reactor composed of a conventional riser and a fluidized bed.

8. The process according to claim 1, wherein the catalytic cracking reactor is a dual diameter riser reactor comprising a pre-lifting section, a first reaction zone, a second reaction zone, and an outlet zone disposed sequentially from bottom to top in a vertical direction that are coaxial and in fluid connection with each other, wherein an inner diameter of the first reaction zone is smaller than that of the second reaction zone, an inner diameter of the second reaction zone is larger than that of the outlet zone, the catalytic cracking catalyst is sent to the pre-lifting section, the catalytic cracking feedstock oil is fed into a lower part of the first reaction zone, the first catalytic cracking reaction is carried out in the first reaction zone, and the second catalytic cracking reaction is carried out in the second reaction zone.

9. The process according to claim 8, wherein a joint region between the first and second reaction zones is provided with at least one quench medium inlet for injecting a quench medium; and/or the second reaction zone is provided with a cooler, with a height of the cooler being 50% to 90% relative to a height of the second reaction zone.

10. The process according to claim 9, wherein the quench medium is selected from the group consisting of a chilling agent, a cooled regenerated catalyst, a cooled semi-regenerated catalyst, a fresh catalyst, and combinations thereof; and wherein the chilling agent is selected from the group consisting of liquefied gases, crude gasolines, stabilized gasolines, light cycle oils, heavy cycle oils, water, and combinations thereof.

11. The process according to claim 1, wherein the cracking active component comprises 10 wt % to 90 wt % of FAU-type zeolite and 10 wt % to 90 wt % of pentasil zeolite, wherein the total amount of the FAU-type zeolite and the pentasil zeolite is 100 wt %, based on the weight of the cracking active component on a dry basis.

12. The process according to claim 1, wherein the step d) further comprises recovering light aromatics from the gasoline fraction by extraction refining using an extraction solvent selected from the group consisting of sulfolane, dimethyl sulfoxide, N-formylmorpholine, tetraethylene glycol, triethylene glycol, N-methylpyridinone, and combinations thereof, at a temperature between 50° C. and 110° C., and a weight ratio of extraction solvent to gasoline fraction between 2 and 6.

13. The process according to claim 1, wherein the catalytic cracking feedstock oil has a polycyclic naphthene content of greater than 40 wt %.

14. The process according to claim 1, wherein the hydrotreatment performed in the pretreating step a) is carried out under a hydrogen partial pressure between 8 MPa and 20 MPa at a reaction temperature between 330° C. and 430° C., a liquid hourly space velocity between 0.2 $h^{-1}$ and 5 $h^{-1}$, and a hydrogen-to-oil ratio by volume between 500 $Nm^3/m^3$ and 2500 $Nm^3/m^3$.

15. The process according to claim 1, wherein the hydrotreatment performed in the pretreating step a) is carried out in the presence of a hydrotreating catalyst comprising a hydrotreating active component and a support, the hydrotreating active component is selected from the group consisting of Group VIB non-noble metals, Group VIII non-noble metals, and combinations thereof, and the support is selected from the group consisting of alumina, silica, amorphous silica-alumina, and combinations thereof.

16. The process according to claim 1, wherein the initial feedstock oil is selected from the group consisting of deep-hydrogenated light cycle oil, coker gas oil from delayed coker, catalytic cracking light cycle oil, catalytic cracking heavy cycle oil, FCC gas oil, slurry oil, hydrocracked diesel oil, residuum hydrocracked diesel oil, wax oil hydrocracked diesel oil, biodiesel, diesel fraction of shale oil, diesel fraction from coal liquefaction, atmospheric overhead oil, distillate oil extracted from atmospheric column, straight-run vacuum gas oil, hydrogenated wax oil, coker gas oil, deasphalted oil, extract oil, raffinate oil, atmospheric residue, vacuum residue, hydrogenated tail oils obtained therefrom by hydrogenation, and combinations thereof.

17. The process according to claim 8, wherein the catalytic cracking product comprises 11-14.5 wt % of isobutane.

18. The process according to claim 17, wherein the catalytic cracking product further comprises 45-59 wt % of gasoline.

* * * * *